(12) United States Patent
Scharf et al.

(10) Patent No.: US 10,989,712 B2
(45) Date of Patent: Apr. 27, 2021

(54) DIAGNOSIS OF A NEUROAUTOIMMUNE DISEASE

(71) Applicant: EUROIMMUN Medizinische Labordiagnostika AG, Luebeck (DE)

(72) Inventors: Madeleine Scharf, Selmsdorf (DE); Lars Komorowski, Ratzeburg (DE); Ramona Miske, Luebeck (DE); Stefanie Hahn, Reinfeld (DE); Yvonne Denno, Luebeck (DE); Christian Probst, Ratzeburg (DE); Farid Benkhadra, Luxembourg (LU)

(73) Assignee: EUROIMMUN MEDIZINISCHE LABORDIAGNOSTIKA AG, Luebeck (DE)

( * ) Notice: Subject to any disclaimer, the term of this patent is extended or adjusted under 35 U.S.C. 154(b) by 0 days.

(21) Appl. No.: 16/582,742

(22) Filed: Sep. 25, 2019

(65) Prior Publication Data

US 2020/0096506 A1    Mar. 26, 2020

(30) Foreign Application Priority Data

Sep. 26, 2018 (EP) .................................... 18196867

(51) Int. Cl.
| | |
|---|---|
| *G01N 33/564* | (2006.01) |
| *C07K 1/22* | (2006.01) |
| *C07K 17/02* | (2006.01) |
| *G01N 33/68* | (2006.01) |

(52) U.S. Cl.
CPC ............. *G01N 33/564* (2013.01); *C07K 1/22* (2013.01); *C07K 17/02* (2013.01); *G01N 33/6896* (2013.01); *G01N 2800/285* (2013.01)

(58) Field of Classification Search
CPC ............. G01N 33/564; G01N 33/6896; G01N 2800/285; G01N 2333/918; G01N 33/53; G01N 33/533; G01N 33/577; C07K 1/22; C07K 17/02; C12Y 301/01; A61K 38/465
See application file for complete search history.

(56) References Cited

U.S. PATENT DOCUMENTS 10,802,024 B2 * 10/2020 Lattwein .............. G01N 33/543

FOREIGN PATENT DOCUMENTS

| EP | 2 952 898 | 12/2015 |
|---|---|---|
| JP | 2002-272478 | 9/2002 |
| WO | 2018/060766 A2 | 4/2018 |
| WO | 2018/060766 A3 | 4/2018 |

OTHER PUBLICATIONS

DAGLA (*Homo sapiens*). NCBI Reference Sequence: NP_006124.1 complied by RefSeq and published Nov. 2010 (Year: 2010).*
European Search Report dated Nov. 14, 2018 in European Application No. 18196867.8.
Bisogno et al., The Journal of Cell Biology, vol. 163, No. 3, Nov. 10, 2003, 463-468.
Pacher et al., Progress in Lipid Research 50 (2011) 193-211.
Popkirov et al., Acta Neuropathologica Communications (2017) 5:40 (10 pages).
Suárez et al., Neuroscience 192 (2011) 112-131.

* cited by examiner

*Primary Examiner* — Kimberly Ballard
*Assistant Examiner* — Stacey N MacFarlane
(74) *Attorney, Agent, or Firm* — Grüneberg and Myers PLLC

(57) ABSTRACT

A method is used for diagnosing a disease by detecting in a sample with antibodies from a patient an autoantibody binding to DAGLA.

6 Claims, 5 Drawing Sheets
(4 of 5 Drawing Sheet(s) Filed in Color)
Specification includes a Sequence Listing.

```
                         SEQUENCE LISTING

<160> NUMBER OF SEQ ID NOS: 28

<210> SEQ ID NO 1
<211> LENGTH: 3129
<212> TYPE: DNA
<213> ORGANISM: Artificial Sequence
<220> FEATURE:
<223> OTHER INFORMATION: cDNA encoding human DAGLA

<400> SEQUENCE: 1
atgcccggga tcgtggtgtt ccggcggcgc tggtctgtgg gcagtgatga cctcgtccta      60
ccagccatct tcctctttct cctgcatacc acctggtttg tgatcctgtc cgtggtgctc     120
ttcggcctgg tctataaccc gcacgaggcc tgctccctga acctggtgga ccacggccgc     180
ggctacctgg gcatcctgct gagctgcatg atcgctgaga tggccatcat ctggctgagc     240
atgcgcgggg gcatcctcta cacggagccc cgtgactcca tgcagtacgt gctctacgtg     300
cgcctggcca tcctggtgat cgagttcatc tacgccatcg tgggcatcgt ctggctcact     360
cagtactaca cctcctgcaa cgacctcact gccaagaatg tcaccctcgg aatggttgtc     420
tgcaactggg tagtcatcct cagtgtgtgc atcactgtcc tctgcgtctt cgaccccacg     480
ggccgcacct ttgtcaagct gagagccacc aagaggaggc agcgtaacct gcggacctac     540
aacctgcggc accgcttaga ggagggtcaa gccaccagct ggtcgcgccg gctcaaagtg     600
ttcctctgct gcacgcggac gaaggactcc cagtcagatg cctactcaga aatcgcctac     660
ctctttgcgg agttcttccg ggaccttgac attgtgccat ccgacatcat tgctggcctg     720
gtgctgctcc ggcagcggca gcgggccaag cgcaacgccg tgctggacga ggcaaacaat     780
gacatcttgg ccttcctgtc tgggatgccg gtgaccagaa acaccaagta cctcgacctc     840
aagaattcac aagagatgct ccgctacaaa gaggtctgct actacatgct ctttgccctg     900
gctgcctacg ggtggcccat gtacctgatg cggaagcccg cctgcggcct gccaactg     960 gctcggtcct gctcgtgttg cctgtgtcct gcgaggccgc ggttcgcccc tggagtcacc    1020
atcgaggaag acaactgctg tggctgtaat gccattgcca tccggcgcca cttcctggac    1080
gagaacatga ctgcggtgga catcgtctat acctcctgcc atgatgcggt ctatgaaacg    1140
cccttctacg tggcggtgga ccatgacaag aagaaagtgg tgatcagtat ccgggggacc    1200
ctgtccccca aggatgccct gactgacctg acgggtgatc tgagcgcct cccgtggag     1260 gggcaccacg gcacctggct gggccacaag ggtatggtcc tctcagctga gtacatcaag    1320
aagaaactgg agcaggagat ggtcctgtcc caggcctttg ggcgagacct gggccgcgga    1380
accaaacact acggcctgat tgtggtgggc cactccctgg gcgcgggcac tgctgccatc    1440
ctctccttcc ttctgcgccc acagtatccg accctcaagt gctttgccta ctccccgcca    1500
gggggcctgc tgagtgagga tgcaatggag tattccaagg agttcgtgac tgctgtggtt    1560
ctgggcaaag acctcgtccc caggattggc ctctctcagc tggaaggctt ccgcagacag    1620
ctcctggatg tcctgcagcg aagcaccaag cccaaatggc ggatcatcgt gggggccacc    1680
aaatgcatcc ccaagtcgga gctgcctgag gaggtagagg tgaccaccct ggccagcacg    1740
cggctctgga cccacccccag cgacctaact atagccctct cagccagcac tccactctac    1800
ccgcccggcc gcatcatcca cgtggtccac aaccaccctg cagagcagtg ctgctgctgt    1860
```

```
gagcaggagg agcccacata ctttgccatc tggggcgaca acaaggcctt caatgaggtg    1920
atcatctcgc cagccatgct gcatgagcac ctgccctatg tggtcatgga ggggctcaac    1980
aaggtgctgg agaactacaa caaggggaag accgctctgc tctctgcagc caaggtcatg    2040
gtgagcccta ccgaggtgga cctgactcct gagctcatct tccagcagca gccactcccc    2100
acggggccgc ccatgcccac tggccttgcc ctggagctgc cgactgcaga ccaccgcaac    2160
agcagcgtca ggagcaagtc ccagtctgag atgagcctgg agggcttctc ggaggggcgg    2220
ctgctgtcgc cagtggttgc ggcggcggcc cgccaggacc cggtggagct gctgctgctg    2280
tctacccagg agcggctggc ggcggagctg caggcccggc gggcaccact ggccaccatg    2340
gagagcctct cggacactga gtccctgtac agcttcgact cgcgccgctc ctcaggcttc    2400
cgcagcatcc ggggctcccc cagcctccac gctgtgctgg agcgtgatga aggccacctc    2460
ttctacattg accctgccat ccccgaggaa aacccatccc tgagctcgcg cactgagctg    2520
ctggcggccg acagcctgtc caagcactca caggacacgc agcccctgga ggcggccctg    2580
ggcagtggcg gcgtcactcc tgagcggccc cccagtgctg cggccaatga cgaggaggaa    2640
gaggttggcg gtgggggtgg cgggccggcc tcccgcgggg agctggcgct gcacaatggg    2700
cgcctggggg actcgcccag tcctcaggtg ctggaattcg ccgagttcat cgacagcctc    2760
ttcaacctgg acagcaagag cagctccttc caagacctct actgcatggt ggtgcccgag    2820
agccccacca gtgactacgc tgagggcccc aagtccccca gccagcaaga gatcctgctc    2880
cgtgcccagt tcgagcccaa cctggtgccc aagcccccac ggctctttgc cggctcagcc    2940 gaccctcct cgggcatctc actctcgccc tccttcccgc tcagctcctc gggtgagctc    3000
atggacctga cgcccacggg cctcagtagc caggaatgcc tggcggctga caagatccgg    3060
acttctaccc ccactggcca cggagccagc cccgccaagc aagatgagct ggtcatctca    3120
gcacgctag                                                           3129
```

<210> SEQ ID NO 2
<211> LENGTH: 35
<212> TYPE: DNA
<213> ORGANISM: Artificial Sequence
<220> FEATURE:
<223> OTHER INFORMATION: sense DAGLA primer for amplifying cDNA
<400> SEQUENCE: 2
atacgtctca catgcccggg atcgtggtgt tccgg                                35

<210> SEQ ID NO 3
<211> LENGTH: 39
<212> TYPE: DNA
<213> ORGANISM: Artificial Sequence
<220> FEATURE:
<223> OTHER INFORMATION: asense DAGLA-Stop primer for amplifying cDNA
<400> SEQUENCE: 3
atacgtctcc tcgagctagc gtgctgagat gaccagctc                            39

<210> SEQ ID NO 4
<211> LENGTH: 1042
<212> TYPE: PRT
<213> ORGANISM: Artificial Sequence
<220> FEATURE:
<223> OTHER INFORMATION: DAGLA as expressed in HEK293

<400> SEQUENCE: 4

```
Met Pro Gly Ile Val Phe Arg Arg Arg Trp Ser Val Gly Ser Asp
1               5                   10                  15

Asp Leu Val Leu Pro Ala Ile Phe Leu Phe Leu Leu His Thr Thr Trp
            20                  25                  30

Phe Val Ile Leu Ser Val Val Leu Phe Gly Leu Val Tyr Asn Pro His
            35                  40                  45

Glu Ala Cys Ser Leu Asn Leu Val Asp His Gly Arg Gly Tyr Leu Gly
            50                  55                  60

Ile Leu Leu Ser Cys Met Ile Ala Glu Met Ala Ile Ile Trp Leu Ser
65                  70                  75                  80

Met Arg Gly Gly Ile Leu Tyr Thr Glu Pro Arg Asp Ser Met Gln Tyr
                85                  90                  95

Val Leu Tyr Val Arg Leu Ala Ile Leu Val Ile Glu Phe Ile Tyr Ala
            100                 105                 110

Ile Val Gly Ile Val Trp Leu Thr Gln Tyr Tyr Thr Ser Cys Asn Asp
            115                 120                 125

Leu Thr Ala Lys Asn Val Thr Leu Gly Met Val Val Cys Asn Trp Val
        130                 135                 140

Val Ile Leu Ser Val Cys Ile Thr Val Leu Cys Val Phe Asp Pro Thr
145                 150                 155                 160

Gly Arg Thr Phe Val Lys Leu Arg Ala Thr Lys Arg Arg Gln Arg Asn
                165                 170                 175

Leu Arg Thr Tyr Asn Leu Arg His Arg Leu Glu Glu Gly Gln Ala Thr
            180                 185                 190

Ser Trp Ser Arg Arg Leu Lys Val Phe Leu Cys Cys Thr Arg Thr Lys
        195                 200                 205

Asp Ser Gln Ser Asp Ala Tyr Ser Glu Ile Ala Tyr Leu Phe Ala Glu
    210                 215                 220

Phe Phe Arg Asp Leu Asp Ile Val Pro Ser Asp Ile Ile Ala Gly Leu
225                 230                 235                 240

Val Leu Leu Arg Gln Arg Gln Arg Ala Lys Arg Asn Ala Val Leu Asp
                245                 250                 255

Glu Ala Asn Asn Asp Ile Leu Ala Phe Leu Ser Gly Met Pro Val Thr
            260                 265                 270

Arg Asn Thr Lys Tyr Leu Asp Leu Lys Asn Ser Gln Glu Met Leu Arg
        275                 280                 285

Tyr Lys Glu Val Cys Tyr Tyr Met Leu Phe Ala Leu Ala Ala Tyr Gly
    290                 295                 300

Trp Pro Met Tyr Leu Met Arg Lys Pro Ala Cys Gly Leu Cys Gln Leu
305                 310                 315                 320

Ala Arg Ser Cys Ser Cys Cys Leu Cys Pro Ala Arg Pro Arg Phe Ala
                325                 330                 335

Pro Gly Val Thr Ile Glu Glu Asp Asn Cys Cys Gly Cys Asn Ala Ile
            340                 345                 350

Ala Ile Arg Arg His Phe Leu Asp Glu Asn Met Thr Ala Val Asp Ile
        355                 360                 365

Val Tyr Thr Ser Cys His Asp Ala Val Tyr Glu Thr Pro Phe Tyr Val
    370                 375                 380

Ala Val Asp His Asp Lys Lys Val Val Ile Ser Ile Arg Gly Thr
385                 390                 395                 400

Leu Ser Pro Lys Asp Ala Leu Thr Asp Leu Thr Gly Asp Ala Glu Arg
            405                 410                 415

Leu Pro Val Glu Gly His His Gly Thr Trp Leu Gly His Lys Gly Met
```

```
            420             425             430
Val Leu Ser Ala Glu Tyr Ile Lys Lys Leu Glu Gln Glu Met Val
            435             440             445
Leu Ser Gln Ala Phe Gly Arg Asp Leu Gly Arg Gly Thr Lys His Tyr
        450             455             460
Gly Leu Ile Val Val Gly His Ser Leu Gly Ala Gly Thr Ala Ala Ile
465             470             475             480
Leu Ser Phe Leu Leu Arg Pro Gln Tyr Pro Thr Leu Lys Cys Phe Ala
                485             490             495
Tyr Ser Pro Pro Gly Leu Leu Ser Glu Asp Ala Met Glu Tyr Ser
            500             505             510
Lys Glu Phe Val Thr Ala Val Leu Gly Lys Asp Leu Val Pro Arg
            515             520             525
Ile Gly Leu Ser Gln Leu Glu Gly Phe Arg Arg Gln Leu Leu Asp Val
            530             535             540
Leu Gln Arg Ser Thr Lys Pro Lys Trp Arg Ile Ile Val Gly Ala Thr
545             550             555             560
Lys Cys Ile Pro Lys Ser Glu Leu Pro Glu Glu Val Glu Val Thr Thr
                565             570             575
Leu Ala Ser Thr Arg Leu Trp Thr His Pro Ser Asp Leu Thr Ile Ala
            580             585             590
Leu Ser Ala Ser Thr Pro Leu Tyr Pro Pro Gly Arg Ile Ile His Val
            595             600             605
Val His Asn His Pro Ala Glu Gln Cys Cys Cys Glu Gln Glu Glu
            610             615             620
Pro Thr Tyr Phe Ala Ile Trp Gly Asp Asn Lys Ala Phe Asn Glu Val
625             630             635             640
Ile Ile Ser Pro Ala Met Leu His Glu His Leu Pro Tyr Val Val Met
                645             650             655
Glu Gly Leu Asn Lys Val Leu Glu Asn Tyr Asn Lys Gly Lys Thr Ala
            660             665             670
Leu Leu Ser Ala Ala Lys Val Met Val Ser Pro Thr Glu Val Asp Leu
            675             680             685
Thr Pro Glu Leu Ile Phe Gln Gln Pro Leu Pro Thr Gly Pro Pro
            690             695             700
Met Pro Thr Gly Leu Ala Leu Glu Leu Pro Thr Ala Asp His Arg Asn
705             710             715             720
Ser Ser Val Arg Ser Lys Ser Gln Ser Glu Met Ser Leu Glu Gly Phe
                725             730             735
Ser Glu Gly Arg Leu Leu Ser Pro Val Val Ala Ala Ala Arg Gln
            740             745             750
Asp Pro Val Glu Leu Leu Leu Ser Thr Gln Glu Arg Leu Ala Ala
            755             760             765
Glu Leu Gln Ala Arg Arg Ala Pro Leu Ala Thr Met Glu Ser Leu Ser
            770             775             780
Asp Thr Glu Ser Leu Tyr Ser Phe Asp Ser Arg Arg Ser Ser Gly Phe
785             790             795             800
Arg Ser Ile Arg Gly Ser Pro Ser Leu His Ala Val Leu Glu Arg Asp
                805             810             815
Glu Gly His Leu Phe Tyr Ile Asp Pro Ala Ile Pro Glu Glu Asn Pro
            820             825             830
Ser Leu Ser Ser Arg Thr Glu Leu Leu Ala Ala Asp Ser Leu Ser Lys
            835             840             845
```

His Ser Gln Asp Thr Gln Pro Leu Glu Ala Ala Leu Gly Ser Gly Gly
    850                 855                 860

Val Thr Pro Glu Arg Pro Ser Ala Ala Ala Asn Asp Glu Glu Glu
865                 870                 875                 880

Glu Val Gly Gly Gly Gly Gly Pro Ala Ser Arg Gly Glu Leu Ala
                885                 890                 895

Leu His Asn Gly Arg Leu Gly Asp Ser Pro Ser Pro Gln Val Leu Glu
                900                 905                 910

Phe Ala Glu Phe Ile Asp Ser Leu Phe Asn Leu Asp Ser Lys Ser Ser
            915                 920                 925

Ser Phe Gln Asp Leu Tyr Cys Met Val Val Pro Glu Ser Pro Thr Ser
    930                 935                 940

Asp Tyr Ala Glu Gly Pro Lys Ser Pro Ser Gln Gln Glu Ile Leu Leu
945                 950                 955                 960

Arg Ala Gln Phe Glu Pro Asn Leu Val Pro Lys Pro Arg Leu Phe
                965                 970                 975

Ala Gly Ser Ala Asp Pro Ser Ser Gly Ile Ser Leu Ser Pro Ser Phe
                980                 985                 990

Pro Leu Ser Ser Ser Gly Glu Leu  Met Asp Leu Thr Pro  Thr Gly Leu
        995                 1000                1005

Ser Ser  Gln Glu Cys Leu Ala  Ala Asp Lys Ile Arg  Thr Ser Thr
    1010                1015                1020

Pro Thr  Gly His Gly Ala Ser  Pro Ala Lys Gln Asp  Glu Leu Val
    1025                1030                1035

Ile Ser  Ala Arg
    1040

<210> SEQ ID NO 5
<211> LENGTH: 73
<212> TYPE: DNA
<213> ORGANISM: Artificial Sequence
<220> FEATURE:
<223> OTHER INFORMATION: sense DAGLA[1-22] primer for cloning DAGLA
      fragment

<400> SEQUENCE: 5
catgcccggg atcgtggtgt tccggcggcg ctggtctgtg ggcagtgatg acctcgtcct    60
accagcctaa tga                                                      73

<210> SEQ ID NO 6
<211> LENGTH: 73
<212> TYPE: DNA
<213> ORGANISM: Artificial Sequence
<220> FEATURE:
<223> OTHER INFORMATION: asense DAGLA[1-22] primer for cloning DAGLA
      fragment

<400> SEQUENCE: 6
tcgatcatta ggctggtagg acgaggtcat cactgcccac agaccagcgc cgccggaaca    60
ccacgatccc ggg                                                      73

<210> SEQ ID NO 7
<211> LENGTH: 61
<212> TYPE: DNA
<213> ORGANISM: Artificial Sequence
<220> FEATURE:
<223> OTHER INFORMATION: sense DAGLA[44-60] primer for cloning DAGLA
      fragment

<400> SEQUENCE: 7
catggtctat aacccgcacg aggcctgctc cctgaacctg gtggaccacg gccgctaatg       60
a                                                                      61

<210> SEQ ID NO 8
<211> LENGTH: 61
<212> TYPE: DNA
<213> ORGANISM: Artificial Sequence
<220> FEATURE:
<223> OTHER INFORMATION: asense DAGLA[44-60] primer for cloning DAGLA
      fragment

<400> SEQUENCE: 8
tcgatcatta gcggccgtgg tccaccaggt tcagggagca ggcctcgtgc gggttataga       60
c                                                                      61

<210> SEQ ID NO 9
<211> LENGTH: 70
<212> TYPE: DNA
<213> ORGANISM: Artificial Sequence
<220> FEATURE:
<223> OTHER INFORMATION: sense DAGLA[81-101] primer for cloning DAGLA
      fragment

<400> SEQUENCE: 9
catgcgcggg ggcatcctct acacggagcc ccgtgactcc atgcagtacg tgctctacgt       60
gcgctaatga                                                             70

<210> SEQ ID NO 10
<211> LENGTH: 70
<212> TYPE: DNA
<213> ORGANISM: Artificial Sequence
<220> FEATURE:
<223> OTHER INFORMATION: asense DAGLA[81-101] primer for cloning DAGLA
      fragment

<400> SEQUENCE: 10
tcgatcatta gcgcacgtag agcacgtact gcatggagtc acgggctcc gtgtagagga       60 tgcccccgcg                                                             70

<210> SEQ ID NO 11
<211> LENGTH: 52
<212> TYPE: DNA
<213> ORGANISM: Artificial Sequence
<220> FEATURE:
<223> OTHER INFORMATION: sense DAGLA[123-136] primer for cloning DAGLA
      fragment

<400> SEQUENCE: 11
catgtacacc tcctgcaacg acctcactgc caagaatgtc accctctaat ga              52

<210> SEQ ID NO 12
<211> LENGTH: 52
<212> TYPE: DNA
<213> ORGANISM: Artificial Sequence
<220> FEATURE:
<223> OTHER INFORMATION: asense DAGLA[123-136] primer for cloning DAGLA
      fragment

<400> SEQUENCE: 12
tcgatcatta gagggtgaca ttcttggcag tgaggtcgtt gcaggaggtg ta              52

<210> SEQ ID NO 13

<211> LENGTH: 259
<212> TYPE: PRT
<213> ORGANISM: Artificial Sequence
<220> FEATURE:
<223> OTHER INFORMATION: H8-GST-DAGLA[1-22]

<400> SEQUENCE: 13

Met Ser His His His His His His His Met Ser Pro Ile Leu Gly
1               5                   10                  15
Tyr Trp Lys Ile Lys Gly Leu Val Gln Pro Thr Arg Leu Leu Leu Glu
            20                  25                  30
Tyr Leu Glu Glu Lys Tyr Glu Glu His Leu Tyr Glu Arg Asp Glu Gly
        35                  40                  45
Asp Lys Trp Arg Asn Lys Lys Phe Glu Leu Gly Leu Glu Phe Pro Asn
    50                  55                  60
Leu Pro Tyr Tyr Ile Asp Gly Asp Val Lys Leu Thr Gln Ser Met Ala
65                  70                  75                  80
Ile Ile Arg Tyr Ile Ala Asp Lys His Asn Met Leu Gly Gly Cys Pro
                85                  90                  95
Lys Glu Arg Ala Glu Ile Ser Met Leu Glu Gly Ala Val Leu Asp Ile
            100                 105                 110
Arg Tyr Gly Val Ser Arg Ile Ala Tyr Ser Lys Asp Phe Glu Thr Leu
        115                 120                 125
Lys Val Asp Phe Leu Ser Lys Leu Pro Glu Met Leu Lys Met Phe Glu
    130                 135                 140
Asp Arg Leu Cys His Lys Thr Tyr Leu Asn Gly Asp His Val Thr His
145                 150                 155                 160
Pro Asp Phe Met Leu Tyr Asp Ala Leu Asp Val Val Leu Tyr Met Asp
                165                 170                 175
Pro Met Cys Leu Asp Ala Phe Pro Lys Leu Val Cys Phe Lys Lys Arg
            180                 185                 190
Ile Glu Ala Ile Pro Gln Ile Asp Lys Tyr Leu Lys Ser Ser Lys Tyr
        195                 200                 205
Ile Ala Trp Pro Leu Gln Gly Trp Gln Ala Thr Phe Gly Gly Gly Asp
    210                 215                 220
His Pro Pro Lys Leu Glu Val Leu Phe Gln Gly Pro Ala Met Pro Gly
225                 230                 235                 240
Ile Val Val Phe Arg Arg Arg Trp Ser Val Gly Ser Asp Asp Leu Val
                245                 250                 255
Leu Pro Ala

<210> SEQ ID NO 14
<211> LENGTH: 255
<212> TYPE: PRT
<213> ORGANISM: Artificial Sequence
<220> FEATURE:
<223> OTHER INFORMATION: H8-GST-DAGLA[44-60]

<400> SEQUENCE: 14

Met Ser His His His His His His His Met Ser Pro Ile Leu Gly
1               5                   10                  15
Tyr Trp Lys Ile Lys Gly Leu Val Gln Pro Thr Arg Leu Leu Leu Glu
            20                  25                  30
Tyr Leu Glu Glu Lys Tyr Glu Glu His Leu Tyr Glu Arg Asp Glu Gly
        35                  40                  45
Asp Lys Trp Arg Asn Lys Lys Phe Glu Leu Gly Leu Glu Phe Pro Asn
    50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
            115                 120                 125

Lys Val Asp Phe Leu Ser Lys Leu Pro Glu Met Leu Lys Met Phe Glu
        130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
            195                 200                 205

Ile Ala Trp Pro Leu Gln Gly Trp Gln Ala Thr Phe Gly Gly Gly Asp
        210                 215                 220

His Pro Pro Lys Leu Glu Val Leu Phe Gln Gly Pro Ala Met Val Tyr
225                 230                 235                 240

Asn Pro His Glu Ala Cys Ser Leu Asn Leu Val Asp His Gly Arg
                245                 250                 255

<210> SEQ ID NO 15
<211> LENGTH: 258
<212> TYPE: PRT
<213> ORGANISM: Artificial Sequence
<220> FEATURE:
<223> OTHER INFORMATION: H8-GST-DAGLA[81-101]

<400> SEQUENCE: 15

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
                20                  25                  30

Tyr Leu Glu Glu Lys Tyr Glu Glu His Leu Tyr Glu Arg Asp Glu Gly
            35                  40                  45

Asp Lys Trp Arg Asn Lys Lys Phe Glu Leu Gly Leu Glu Phe Pro Asn
        50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
            115                 120                 125

Lys Val Asp Phe Leu Ser Lys Leu Pro Glu Met Leu Lys Met Phe Glu
        130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

```
Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
            195                 200                 205

Ile Ala Trp Pro Leu Gln Gly Trp Gln Ala Thr Phe Gly Gly Gly Asp
            210                 215                 220

His Pro Pro Lys Leu Glu Val Leu Phe Gln Gly Pro Ala Met Arg Gly
225                 230                 235                 240

Gly Ile Leu Tyr Thr Glu Pro Arg Asp Ser Met Gln Tyr Val Leu Tyr
                245                 250                 255

Val Arg

<210> SEQ ID NO 16
<211> LENGTH: 252
<212> TYPE: PRT
<213> ORGANISM: Artificial Sequence
<220> FEATURE:
<223> OTHER INFORMATION: H8-GST-DAGLA[123-136]

<400> SEQUENCE: 16

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
            20                  25                  30

Tyr Leu Glu Glu Lys Tyr Glu Glu His Leu Tyr Glu Arg Asp Glu Gly
            35                  40                  45

Asp Lys Trp Arg Asn Lys Lys Phe Glu Leu Gly Leu Glu Phe Pro Asn
50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
            115                 120                 125

Lys Val Asp Phe Leu Ser Lys Leu Pro Glu Met Leu Lys Met Phe Glu
130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
            195                 200                 205

Ile Ala Trp Pro Leu Gln Gly Trp Gln Ala Thr Phe Gly Gly Gly Asp
            210                 215                 220

His Pro Pro Lys Leu Glu Val Leu Phe Gln Gly Pro Ala Met Tyr Thr
225                 230                 235                 240

Ser Cys Asn Asp Leu Thr Ala Lys Asn Val Thr Leu
                245                 250

<210> SEQ ID NO 17
<211> LENGTH: 41
```

```
<212> TYPE: DNA
<213> ORGANISM: Artificial Sequence
<220> FEATURE:
<223> OTHER INFORMATION: sense DAGLA[158-598]

<400> SEQUENCE: 17
atacgtctcg catggacccc acgggccgca cctttgtcaa g                          41

<210> SEQ ID NO 18
<211> LENGTH: 46
<212> TYPE: DNA
<213> ORGANISM: Artificial Sequence
<220> FEATURE:
<223> OTHER INFORMATION: asense DAGLA[158-598]

<400> SEQUENCE: 18
tatcgtctcg tcgatcatta tggagtgctg gctgagaggg ctatag                    46

<210> SEQ ID NO 19
<211> LENGTH: 43
<212> TYPE: DNA
<213> ORGANISM: Artificial Sequence
<220> FEATURE:
<223> OTHER INFORMATION: sense DAGLA[583-1042]

<400> SEQUENCE: 19
atacgtctcg catgtggacc caccccagcg acctaactat agc                        43

<210> SEQ ID NO 20
<211> LENGTH: 47
<212> TYPE: DNA
<213> ORGANISM: Artificial Sequence
<220> FEATURE:
<223> OTHER INFORMATION: asense DAGLA[583-1042]

<400> SEQUENCE: 20
tatcgtctcg tcgatcatta gcgtgctgag atgaccagct catcttg                   47

<210> SEQ ID NO 21
<211> LENGTH: 453
<212> TYPE: PRT
<213> ORGANISM: Artificial Sequence
<220> FEATURE:
<223> OTHER INFORMATION: H8-DAGLA[158-598]

<400> SEQUENCE: 21

Met Ser His His His His His His His Ser Met Asp Pro Thr Gly
1               5                   10                  15

Arg Thr Phe Val Lys Leu Arg Ala Thr Lys Arg Gln Arg Asn Leu
                20                  25                  30

Arg Thr Tyr Asn Leu Arg His Arg Leu Glu Glu Gly Gln Ala Thr Ser
            35                  40                  45

Trp Ser Arg Arg Leu Lys Val Phe Leu Cys Cys Thr Arg Thr Lys Asp
 50                  55                  60

Ser Gln Ser Asp Ala Tyr Ser Glu Ile Ala Tyr Leu Phe Ala Glu Phe
65                  70                  75                  80

Phe Arg Asp Leu Asp Ile Val Pro Ser Asp Ile Ile Ala Gly Leu Val
                85                  90                  95

Leu Leu Arg Gln Arg Gln Arg Ala Lys Arg Asn Ala Val Leu Asp Glu
            100                 105                 110

Ala Asn Asn Asp Ile Leu Ala Phe Leu Ser Gly Met Pro Val Thr Arg
        115                 120                 125
```

```
Asn Thr Lys Tyr Leu Asp Leu Lys Asn Ser Gln Glu Met Leu Arg Tyr
    130                 135                 140

Lys Glu Val Cys Tyr Tyr Met Leu Phe Ala Leu Ala Ala Tyr Gly Trp
145                 150                 155                 160

Pro Met Tyr Leu Met Arg Lys Pro Ala Cys Gly Leu Cys Gln Leu Ala
                165                 170                 175

Arg Ser Cys Ser Cys Leu Cys Pro Ala Arg Pro Arg Phe Ala Pro
            180                 185                 190

Gly Val Thr Ile Glu Glu Asp Asn Cys Gly Cys Asn Ala Ile Ala
                195                 200                 205

Ile Arg Arg His Phe Leu Asp Glu Asn Met Thr Ala Val Asp Ile Val
    210                 215                 220

Tyr Thr Ser Cys His Asp Ala Val Tyr Glu Thr Pro Phe Tyr Val Ala
225                 230                 235                 240

Val Asp His Asp Lys Lys Val Val Ile Ser Ile Arg Gly Thr Leu
                245                 250                 255

Ser Pro Lys Asp Ala Leu Thr Asp Leu Thr Gly Asp Ala Glu Arg Leu
                260                 265                 270

Pro Val Glu Gly His His Gly Thr Trp Leu Gly His Lys Gly Met Val
    275                 280                 285

Leu Ser Ala Glu Tyr Ile Lys Lys Leu Glu Gln Glu Met Val Leu
    290                 295                 300

Ser Gln Ala Phe Gly Arg Asp Leu Gly Arg Gly Thr Lys His Tyr Gly
305                 310                 315                 320

Leu Ile Val Val Gly His Ser Leu Gly Ala Gly Thr Ala Ala Ile Leu
                325                 330                 335

Ser Phe Leu Leu Arg Pro Gln Tyr Pro Thr Leu Lys Cys Phe Ala Tyr
                340                 345                 350

Ser Pro Pro Gly Gly Leu Leu Ser Glu Asp Ala Met Glu Tyr Ser Lys
                355                 360                 365

Glu Phe Val Thr Ala Val Val Leu Gly Lys Asp Leu Val Pro Arg Ile
370                 375                 380

Gly Leu Ser Gln Leu Glu Gly Phe Arg Arg Gln Leu Leu Asp Val Leu
385                 390                 395                 400

Gln Arg Ser Thr Lys Pro Lys Trp Arg Ile Ile Val Gly Ala Thr Lys
                405                 410                 415

Cys Ile Pro Lys Ser Glu Leu Pro Glu Val Glu Val Thr Thr Leu
                420                 425                 430

Ala Ser Thr Arg Leu Trp Thr His Pro Ser Asp Leu Thr Ile Ala Leu
                435                 440                 445

Ser Ala Ser Thr Pro
        450

<210> SEQ ID NO 22
<211> LENGTH: 472
<212> TYPE: PRT
<213> ORGANISM: Artificial Sequence
<220> FEATURE:
<223> OTHER INFORMATION: H8-DAGLA[583-1042]

<400> SEQUENCE: 22

Met Ser His His His His His His Ser Met Trp Thr His Pro
1               5                   10                  15

Ser Asp Leu Thr Ile Ala Leu Ser Ala Ser Thr Pro Leu Tyr Pro Pro
                20                  25                  30
```

```
Gly Arg Ile Ile His Val Val His Asn His Pro Ala Glu Gln Cys Cys
             35                  40                  45

Cys Cys Glu Gln Glu Glu Pro Thr Tyr Phe Ala Ile Trp Gly Asp Asn
 50                  55                  60

Lys Ala Phe Asn Glu Val Ile Ile Ser Pro Ala Met Leu His Glu His
 65                  70                  75                  80

Leu Pro Tyr Val Val Met Gly Leu Asn Lys Val Leu Glu Asn Tyr
                 85                  90                  95

Asn Lys Gly Lys Thr Ala Leu Leu Ser Ala Ala Lys Val Met Val Ser
                100                 105                 110

Pro Thr Glu Val Asp Leu Thr Pro Glu Leu Ile Phe Gln Gln Gln Pro
                115                 120                 125

Leu Pro Thr Gly Pro Pro Met Pro Thr Gly Leu Ala Leu Glu Leu Pro
130                 135                 140

Thr Ala Asp His Arg Asn Ser Ser Val Arg Ser Lys Ser Gln Ser Glu
145                 150                 155                 160

Met Ser Leu Glu Gly Phe Ser Glu Gly Arg Leu Leu Ser Pro Val Val
                165                 170                 175

Ala Ala Ala Ala Arg Gln Asp Pro Val Glu Leu Leu Leu Leu Ser Thr
                180                 185                 190

Gln Glu Arg Leu Ala Ala Glu Leu Gln Ala Arg Arg Ala Pro Leu Ala
                195                 200                 205

Thr Met Glu Ser Leu Ser Asp Thr Glu Ser Leu Tyr Ser Phe Asp Ser
210                 215                 220

Arg Arg Ser Ser Gly Phe Arg Ser Ile Arg Gly Ser Pro Ser Leu His
225                 230                 235                 240

Ala Val Leu Glu Arg Asp Glu Gly His Leu Phe Tyr Ile Asp Pro Ala
                245                 250                 255

Ile Pro Glu Glu Asn Pro Ser Leu Ser Ser Arg Thr Glu Leu Leu Ala
                260                 265                 270

Ala Asp Ser Leu Ser Lys His Ser Gln Asp Thr Gln Pro Leu Glu Ala
                275                 280                 285

Ala Leu Gly Ser Gly Val Thr Pro Glu Arg Pro Pro Ser Ala Ala
290                 295                 300

Ala Asn Asp Glu Glu Glu Val Gly Gly Gly Gly Gly Pro Ala
305                 310                 315                 320

Ser Arg Gly Glu Leu Ala Leu His Asn Gly Arg Leu Gly Asp Ser Pro
                325                 330                 335

Ser Pro Gln Val Leu Glu Phe Ala Glu Phe Ile Asp Ser Leu Phe Asn
                340                 345                 350

Leu Asp Ser Lys Ser Ser Ser Phe Gln Asp Leu Tyr Cys Met Val Val
                355                 360                 365

Pro Glu Ser Pro Thr Ser Asp Tyr Ala Glu Gly Pro Lys Ser Pro Ser
370                 375                 380

Gln Gln Glu Ile Leu Leu Arg Ala Gln Phe Glu Pro Asn Leu Val Pro
385                 390                 395                 400

Lys Pro Pro Arg Leu Phe Ala Gly Ser Ala Asp Pro Ser Ser Gly Ile
                405                 410                 415

Ser Leu Ser Pro Ser Phe Pro Leu Ser Ser Gly Glu Leu Met Asp
                420                 425                 430

Leu Thr Pro Thr Gly Leu Ser Ser Gln Glu Cys Leu Ala Ala Asp Lys
                435                 440                 445

Ile Arg Thr Ser Thr Pro Thr Gly His Gly Ala Ser Pro Ala Lys Gln
```

Asp Glu Leu Val Ile Ser Ala Arg
465             470

<210> SEQ ID NO 23
<211> LENGTH: 22
<212> TYPE: PRT
<213> ORGANISM: Artificial Sequence
<220> FEATURE:
<223> OTHER INFORMATION: H8-GST-DAGLA[1-22]

<400> SEQUENCE: 23

Met Pro Gly Ile Val Val Phe Arg Arg Arg Trp Ser Val Gly Ser Asp
1               5                   10                  15

Asp Leu Val Leu Pro Ala
            20

<210> SEQ ID NO 24
<211> LENGTH: 17
<212> TYPE: PRT
<213> ORGANISM: Artificial Sequence
<220> FEATURE:
<223> OTHER INFORMATION: H8-GST-DAGLA[44-60]

<400> SEQUENCE: 24

Val Tyr Asn Pro His Glu Ala Cys Ser Leu Asn Leu Val Asp His Gly
1               5                   10                  15

Arg

<210> SEQ ID NO 25
<211> LENGTH: 21
<212> TYPE: PRT
<213> ORGANISM: Artificial Sequence
<220> FEATURE:
<223> OTHER INFORMATION: H8-GST-DAGLA[81-101]

<400> SEQUENCE: 25

Met Arg Gly Gly Ile Leu Tyr Thr Glu Pro Arg Asp Ser Met Gln Tyr
1               5                   10                  15

Val Leu Tyr Val Arg
            20

<210> SEQ ID NO 26
<211> LENGTH: 14
<212> TYPE: PRT
<213> ORGANISM: Artificial Sequence
<220> FEATURE:
<223> OTHER INFORMATION: H8-GST-DAGLA[123-136], reactive with patient
      sera

<400> SEQUENCE: 26

Tyr Thr Ser Cys Asn Asp Leu Thr Ala Lys Asn Val Thr Leu
1               5                   10

<210> SEQ ID NO 27
<211> LENGTH: 441
<212> TYPE: PRT
<213> ORGANISM: Artificial Sequence
<220> FEATURE:
<223> OTHER INFORMATION: DAGLA[158-598]

<400> SEQUENCE: 27

Thr Gly Arg Thr Phe Val Lys Leu Arg Ala Thr Lys Arg Arg Gln Arg
1               5                   10                  15

-continued

Asn Leu Arg Thr Tyr Asn Leu Arg His Arg Leu Glu Glu Gly Gln Ala
            20                  25                  30

Thr Ser Trp Ser Arg Arg Leu Lys Val Phe Leu Cys Cys Thr Arg Thr
        35                  40                  45

Lys Asp Ser Gln Ser Asp Ala Tyr Ser Glu Ile Ala Tyr Leu Phe Ala
    50                  55                  60

Glu Phe Phe Arg Asp Leu Asp Ile Val Pro Ser Asp Ile Ile Ala Gly
65                  70                  75                  80

Leu Val Leu Leu Arg Gln Arg Gln Arg Ala Lys Arg Asn Ala Val Leu
                85                  90                  95

Asp Glu Ala Asn Asn Asp Ile Leu Ala Phe Leu Ser Gly Met Pro Val
            100                 105                 110

Thr Arg Asn Thr Lys Tyr Leu Asp Leu Lys Asn Ser Gln Glu Met Leu
        115                 120                 125

Arg Tyr Lys Glu Val Cys Tyr Tyr Met Leu Phe Ala Leu Ala Ala Tyr
    130                 135                 140

Gly Trp Pro Met Tyr Leu Met Arg Lys Pro Ala Cys Gly Leu Cys Gln
145                 150                 155                 160

Leu Ala Arg Ser Cys Ser Cys Cys Leu Cys Pro Ala Arg Pro Arg Phe
                165                 170                 175

Ala Pro Gly Val Thr Ile Glu Glu Asp Asn Cys Cys Gly Cys Asn Ala
            180                 185                 190

Ile Ala Ile Arg Arg His Phe Leu Asp Glu Asn Met Thr Ala Val Asp
        195                 200                 205

Ile Val Tyr Thr Ser Cys His Asp Ala Val Tyr Glu Thr Pro Phe Tyr
    210                 215                 220

Val Ala Val Asp His Asp Lys Lys Val Val Ile Ser Ile Arg Gly
225                 230                 235                 240

Thr Leu Ser Pro Lys Asp Ala Leu Thr Asp Leu Thr Gly Asp Ala Glu
                245                 250                 255

Arg Leu Pro Val Glu Gly His His Gly Thr Trp Leu Gly His Lys Gly
            260                 265                 270

Met Val Leu Ser Ala Glu Tyr Ile Lys Lys Leu Glu Gln Glu Met
        275                 280                 285

Val Leu Ser Gln Ala Phe Gly Arg Asp Leu Gly Arg Gly Thr Lys His
    290                 295                 300

Tyr Gly Leu Ile Val Val Gly His Ser Leu Gly Ala Gly Thr Ala Ala
305                 310                 315                 320

Ile Leu Ser Phe Leu Leu Arg Pro Gln Tyr Pro Thr Leu Lys Cys Phe
                325                 330                 335

Ala Tyr Ser Pro Pro Gly Gly Leu Leu Ser Glu Asp Ala Met Glu Tyr
            340                 345                 350

Ser Lys Glu Phe Val Thr Ala Val Leu Gly Lys Asp Leu Val Pro
        355                 360                 365

Arg Ile Gly Leu Ser Gln Leu Glu Gly Phe Arg Arg Gln Leu Leu Asp
    370                 375                 380

Val Leu Gln Arg Ser Thr Lys Pro Lys Trp Arg Ile Ile Val Gly Ala
385                 390                 395                 400

Thr Lys Cys Ile Pro Lys Ser Glu Leu Pro Glu Val Glu Val Thr
                405                 410                 415

Thr Leu Ala Ser Thr Arg Leu Trp Thr His Pro Ser Asp Leu Thr Ile
            420                 425                 430

Ala Leu Ser Ala Ser Thr Pro Pro Asp

-continued

```
            435                 440
```

<210> SEQ ID NO 28
<211> LENGTH: 460
<212> TYPE: PRT
<213> ORGANISM: Artificial Sequence
<220> FEATURE:
<223> OTHER INFORMATION: DAGLA[583-1042], reactive with patient sera

<400> SEQUENCE: 28

```
Trp Thr His Pro Ser Asp Leu Thr Ile Ala Leu Ser Ala Ser Thr Pro
1               5                   10                  15

Leu Tyr Pro Pro Gly Arg Ile Ile His Val Val His Asn His Pro Ala
            20                  25                  30

Glu Gln Cys Cys Cys Cys Glu Gln Glu Glu Pro Thr Tyr Phe Ala Ile
        35                  40                  45

Trp Gly Asp Asn Lys Ala Phe Asn Glu Val Ile Ile Ser Pro Ala Met
    50                  55                  60

Leu His Glu His Leu Pro Tyr Val Val Met Glu Gly Leu Asn Lys Val
65                  70                  75                  80

Leu Glu Asn Tyr Asn Lys Gly Lys Thr Ala Leu Leu Ser Ala Ala Lys
                85                  90                  95

Val Met Val Ser Pro Thr Glu Val Asp Leu Thr Pro Glu Leu Ile Phe
            100                 105                 110

Gln Gln Gln Pro Leu Pro Thr Gly Pro Pro Met Pro Thr Gly Leu Ala
        115                 120                 125

Leu Glu Leu Pro Thr Ala Asp His Arg Asn Ser Ser Val Arg Ser Lys
    130                 135                 140

Ser Gln Ser Glu Met Ser Leu Glu Gly Phe Ser Glu Gly Arg Leu Leu
145                 150                 155                 160

Ser Pro Val Val Ala Ala Ala Arg Gln Asp Pro Val Glu Leu Leu
                165                 170                 175

Leu Leu Ser Thr Gln Glu Arg Leu Ala Ala Glu Leu Gln Ala Arg Arg
            180                 185                 190

Ala Pro Leu Ala Thr Met Glu Ser Leu Ser Asp Thr Glu Ser Leu Tyr
        195                 200                 205

Ser Phe Asp Ser Arg Arg Ser Ser Gly Phe Arg Ser Ile Arg Gly Ser
    210                 215                 220

Pro Ser Leu His Ala Val Leu Glu Arg Asp Glu Gly His Leu Phe Tyr
225                 230                 235                 240

Ile Asp Pro Ala Ile Pro Glu Glu Asn Pro Ser Leu Ser Ser Arg Thr
                245                 250                 255

Glu Leu Leu Ala Ala Asp Ser Leu Ser Lys His Ser Gln Asp Thr Gln
            260                 265                 270

Pro Leu Glu Ala Ala Leu Gly Ser Gly Gly Val Thr Pro Glu Arg Pro
        275                 280                 285

Pro Ser Ala Ala Ala Asn Asp Glu Glu Glu Val Gly Gly Gly Gly
    290                 295                 300

Gly Gly Pro Ala Ser Arg Gly Glu Leu Ala Leu His Asn Gly Arg Leu
305                 310                 315                 320

Gly Asp Ser Pro Ser Pro Gln Val Leu Glu Phe Ala Glu Phe Ile Asp
                325                 330                 335

Ser Leu Phe Asn Leu Asp Ser Lys Ser Ser Ser Phe Gln Asp Leu Tyr
            340                 345                 350

Cys Met Val Val Pro Glu Ser Pro Thr Ser Asp Tyr Ala Glu Gly Pro
```

-continued

```
                355                 360                 365
Lys Ser Pro Ser Gln Gln Glu Ile Leu Leu Arg Ala Gln Phe Glu Pro
        370                 375                 380

Asn Leu Val Pro Lys Pro Pro Arg Leu Phe Ala Gly Ser Ala Asp Pro
385                 390                 395                 400

Ser Ser Gly Ile Ser Leu Ser Pro Ser Phe Pro Leu Ser Ser Ser Gly
                405                 410                 415

Glu Leu Met Asp Leu Thr Pro Thr Gly Leu Ser Ser Gln Glu Cys Leu
            420                 425                 430

Ala Ala Asp Lys Ile Arg Thr Ser Thr Pro Thr Gly His Gly Ala Ser
        435                 440                 445

Pro Ala Lys Gln Asp Glu Leu Val Ile Ser Ala Arg
450                 455                 460
```

DIAGNOSIS OF A NEUROAUTOIMMUNE DISEASE

CROSS-REFERENCE TO RELATED APPLICATIONS

The present application claims the benefit of the European Application EP18196867.8 filed on Sep. 26, 2018, which is incorporated by reference in its entirety.

REFERENCE TO A SEQUENCE LISTING

The present application is accompanied by an ASCII text file as a computer readable form containing the sequence listing, titled "2019-08-26-SEQ-as-filed," created on Aug. 16, 2019, 9:27:39 AM, with the file size of 43,269 bytes, which is incorporated by reference in its entirety. Applicants hereby state that the information recorded in computer readable form is identical to the written (on paper or compact disc) sequence listing.

BACKGROUND OF THE INVENTION

Field of the Invention

The present invention relates to a method for diagnosing a disease comprising the step detecting in a sample comprising antibodies from a patient an autoantibody binding to DAGLA, an immobilized polypeptide comprising DAGLA or a variant thereof, a use of a polypeptide comprising DAGLA or a variant thereof for the diagnosis of a disease, an isolated autoantibody binding to DAGLA, a use of the autoantibody for the diagnosis of a disease, a method for isolating an autoantibody binding DAGLA, a pharmaceutical composition or medical device comprising DAGLA or a variant thereof, a kit for the diagnosis of a disease comprising said polypeptide or said medical device and a use of said polypeptide or autoantibody for the manufacture of a kit or medical device.

Discussion of the Background

Developing diagnostic systems for neurological diseases is a continuing challenge in biomedical science, not in the least because many symptoms encountered may be accounted for by a huge variety of causes including genetically-inherited diseases, drug abuse, malnutrition, infection, injury, psychiatric illness, immunological defects and cancer.

Since a neurological disease is rarely associated with a unique characteristic pattern of clinical symptoms, it is often difficult to provide a reliable diagnosis solely based on the observation and examination of the patients affected or their medical history.

The importance of an early diagnosis cannot be overemphasized. Many neurological disorders, most prominently Alzheimer's and Parkinson's diseases as well as Multiple Sclerosis, cannot be cured, but drugs are available that may be used to slow down their progression. In addition, certain rare types of cancer are associated with neurological symptoms. The earlier the diagnosis, the better the chances to exploit the spectrum of available therapies to the full benefit of the patient.

This holds all the more true in the case of neurological diseases associated with autoantibodies. In some cases, the link between a specific detectable autoantibody and a condition is sufficiently strong to allow for an immediate diagnosis.

But even if it is not, the detection of autoantibodies may point the physician in charge to therapeutic means that may be used to ameliorate the patient's condition. There is a variety of widely used immunosuppressants that may be used regardless of the nature of the autoantibody's target. Alternatively, apheresis may be used to remove autoantibodies from the patient's blood. In many cases, patients went on to lead a normal life following early diagnosis and treatment of a neurological autoimmune disease.

Diagnostic assays based on the detection of autoantibodies may also corroborate the diagnosis of diseases other than those associated with autoantibodies. If it turns out that a blood sample is devoid of specific autoantibodies, this is likely to help the physician in charge exclude a range of possibilities and thus narrow down the spectrum of plausible conditions.

Examples of neurological conditions coinciding with the emergence of autoantibodies include Neuromyelitis optica, a disease characterized by loss of visual perception and spinal cord function, and anti-NMDA receptor encephalitis, which is associated with autonomic dysfunction, hypoventilation, cerebellar ataxia, hemiparesis, loss of consciousness, or catatonia. Whilst the involvement of autoantibodies and the nature of these conditions as such was previously poorly understood, many of this disease can now be diagnosed and treated efficiently owing to the availability of assays based on the detection of autoantibodies.

Therefore, it is paramount that new approaches be developed to distinguish neurological conditions associated with autoantibodies from those that are not.

SUMMARY OF THE INVENTION

The present invention relates to autoantibodies to DAGLA and diagnostic assays based on their detection. As far as the inventors are aware, the existence of autoantibodies to DAGLA, let alone their diagnostic usefulness, has not yet been reported in the state of the art. A number of companies have commercialized recombinant antibodies binding to DAGLA, for example LifeSpan Biosciences, Inc and Sigma.

The problem underlying the present invention is to provide novel reagents, devices and methods that may be used to support the diagnosis and treatment of an autoimmune disease, preferably an autoimmune disease of the nervous system or associated with a neurological disease or neurological symptoms, more preferably selected from the group comprising PNS, cerebellitis, epilepsy and sclerosis.

Another problem underlying the present invention is to provide novel reagents, devices and methods that may be used to distinguish autoimmune diseases, in particular neurological autoimmune diseases, more preferably selected from the group comprising PNS, cerebellitis, epilepsy, ataxia, polyneuropathy and/or polyradiculopathy, and sclerosis, from diseases other than autoimmune diseases, for example from infections associated with neurological symptoms, not in the least to determine the most promising treatment regimen, more specifically whether or not an immunosuppressive treatment is adequate.

The problem underlying the present invention is solved, for example, by the subject-matter of the following embodiments.

1. A method for diagnosing a disease comprising the step detecting in a sample from a patient an autoantibody binding to DAGLA.
2. An immobilized polypeptide comprising DAGLA or a variant thereof.
3. A use of a polypeptide comprising DAGLA or a variant thereof for the diagnosis of a disease, preferably comprising the step detecting in a sample an autoantibody binding to DAGLA.
4. A polypeptide comprising DAGLA or a variant thereof for use in a treatment of a disease.
5. An isolated autoantibody to DAGLA.
6. A use of the autoantibody according to embodiment 5 for the diagnosis of a disease.
7. A method for isolating an autoantibody binding to DAGLA, comprising the steps
    a) contacting a sample comprising the autoantibody with a polypeptide comprising DAGLA or a variant thereof under conditions compatible with formation of a complex, wherein said autoantibody binds to said polypeptide,
    b) isolating the complex formed in step a),
    c1) detecting the complex formed in step a) or c2) dissociating the complex isolated in step b) and separating the autoantibody from the polypeptide.
8. A pharmaceutical composition comprising a polypeptide comprising DAGLA or a variant thereof.
9. A medical device, preferably diagnostic device, comprising a polypeptide comprising DAGLA or a variant thereof.
10. A kit for the diagnosis of a disease, which kit comprises a polypeptide comprising DAGLA or a variant thereof or a medical device comprising a polypeptide comprising DAGLA or a variant thereof,
    wherein preferably the kit comprises in addition a means for detecting a complex comprising the polypeptide and an antibody binding to DAGLA, preferably an autoantibody binding to DAGLA,
    wherein preferably the kit further comprises a positive control comprising DAGLA or a variant thereof.
11. A use of a polypeptide comprising DAGLA or a variant thereof or an autoantibody binding to DAGLA or a medical device comprising a polypeptide comprising DAGLA or a variant thereof for the manufacture of a kit or medical device, preferably diagnostic device, for the diagnosis of a disease.
12. The method, polypeptide, use, autoantibody, pharmaceutical composition, medical device or kit according to any of embodiments 1, 3, 4, 6, 10 and 11,
    wherein the disease is PNS, cerebellitis, epilepsy, sclerosis and a tumor.
13. The method or use according to any of embodiments 1, 3, 7 and 12, wherein the sample is a bodily fluid comprising antibodies, preferably selected from the group comprising whole blood, plasma, serum, cerebrospinal fluid and saliva.
14. The method, use or kit according to any of embodiments 1, 3, 6, 7 and 10 to 13, wherein the autoantibody or complex is detected using a technique selected from the group comprising immunodiffusion techniques, immunoelectrophoretic techniques, light scattering immunoassays, agglutination techniques, labeled immunoassays such as those from the group comprising radiolabeled immunoassay, enzyme immunoassays, more preferably ELISA, chemiluminscence immunoassays, preferably electrochemiluminescence immunoassay, and immunofluorescence, preferably indirect immunofluorescence.
15. The medical device or kit according to any of embodiments 9 to 14, wherein the medical device is selected from the group comprising a glass slide, preferably for microscopy, a biochip, a microtiter plate, a lateral flow device, a test strip, a membrane, preferably a line blot, a chromatography column and a bead, preferably a magnetic or fluorescent bead.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
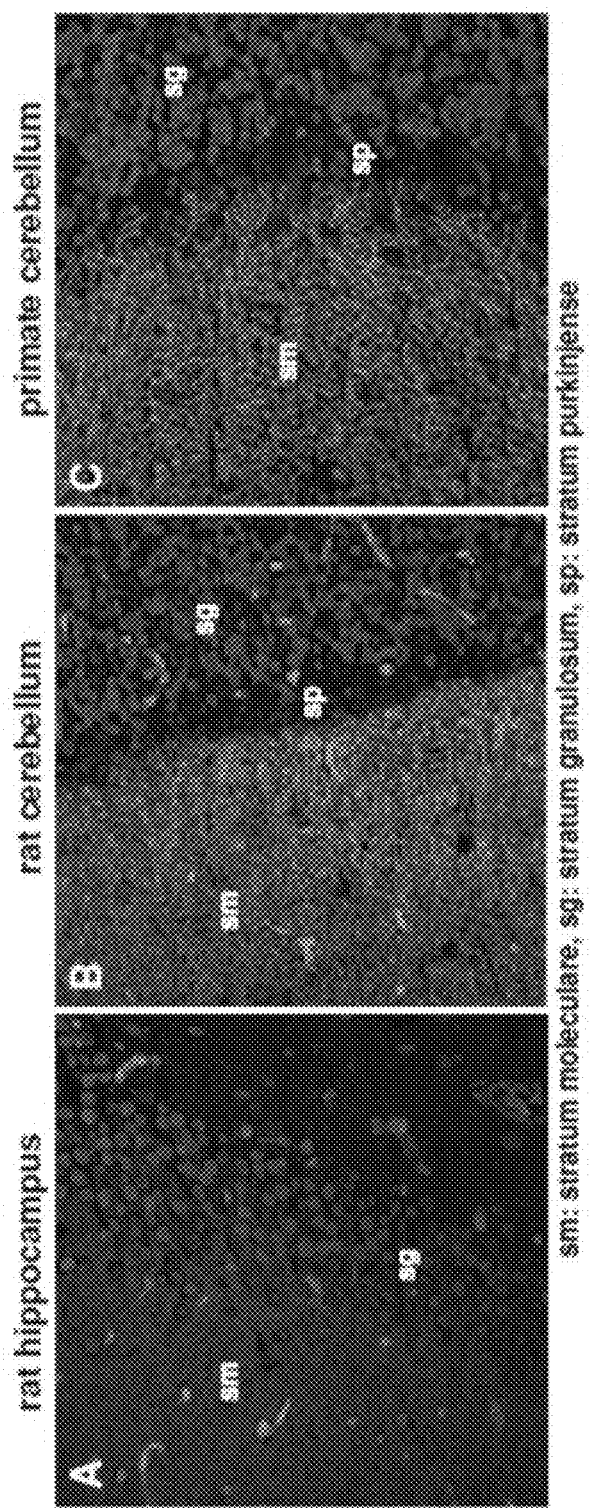
FIG. 1 shows the results of indirect immunofluorescence assays of sera from patients P1 to P5 using permeabilized cryosections of rat and primate cerebellum. Granular staining of the molecular layer was observed.

In a first aspect, the problem is solved by a method for diagnosing a disease comprising the step detecting in a sample from a patient an autoantibody binding to DAGLA.

In a second aspect, the problem is solved by an immobilized polypeptide comprising DAGLA or a variant thereof.

In a third aspect, the problem is solved by a use of a polypeptide comprising DAGLA or a variant thereof for the diagnosis of a disease, preferably comprising the step detecting in a sample an autoantibody binding to DAGLA.

In a $4^{th}$ aspect, the problem is solved by a polypeptide comprising DAGLA or a variant thereof for use in a treatment of a disease.

In a $5^{th}$ aspect, the problem is solved by an autoantibody, preferably an isolated autoantibody to DAGLA.

In a 6th aspect, the problem is solved by a use of the autoantibody according to the present invention for the diagnosis of a disease.

In a 7 aspect, the problem is solved by a method for isolating an autoantibody binding to DAGLA, comprising the steps
a) contacting a sample comprising the autoantibody with a polypeptide comprising DAGLA or a variant thereof under conditions compatible with formation of a complex, wherein said autoantibody binds to said polypeptide,
b) isolating the complex formed in step a),
c1) detecting the complex formed in step a) or c2) dissociating the complex isolated in step b) and separating the autoantibody from the polypeptide.

In an 8th aspect, the problem is solved by a pharmaceutical composition or medical device, preferably diagnostic device, comprising a polypeptide comprising DAGLA or a variant thereof.

In a 9th aspect the problem is solved by a kit for the diagnosis of a disease, which kit comprises a polypeptide comprising DAGLA or a variant thereof or a medical device comprising a polypeptide comprising DAGLA or a variant thereof,
wherein preferably the kit comprises in addition a means for detecting a complex comprising the polypeptide and an antibody binding to DAGLA, preferably an autoantibody binding to DAGLA,
wherein preferably the kit further comprises a positive control comprising DAGLA or a variant thereof or a negative control.

In a 10th aspect, the problem is solved by a use of a polypeptide comprising DAGLA or a variant thereof or an autoantibody binding to DAGLA or a medical device comprising a polypeptide comprising DAGLA or a variant thereof for the manufacture of a kit or medical device, preferably diagnostic device, for the diagnosis of a disease.

In a preferred embodiment, the disease is PNS, preferably associated with a condition selected from the group comprising cerebellitis, epilepsy and sclerosis. In another preferred embodiment, the disease is selected from the group comprising PNS, cerebellitis, epilepsy, sclerosis and a tumor, more preferably PNS, cerebellitis, epilepsy and sclerosis. In a preferred embodiment, the disease is a cancer, preferably from the group comprising a thoracic cancer, more preferably lung cancer or thymus cancer, most preferably from the group comprising small cell lung cancer, carcinoid and non-small cell lung cancer; a breast, gynecologic and testicular cancer; and hematologic malignancies and solid tumors, preferably from the group comprising lymphoma, leukemia, melanoma, urinary tract cancers, gastrointestinal cancers, colon cancer, gastric and esophageal cancers, head and neck cancers, sarcoma and histiocytosis.

In a preferred embodiment, the sample is a bodily fluid comprising antibodies, preferably selected from the group comprising whole blood, plasma, serum, cerebrospinal fluid and saliva.

In a preferred embodiment, the autoantibody or complex is detected using a technique selected from the group comprising immunodiffusion techniques, immunoelectrophoretic techniques, light scattering immunoassays, agglutination techniques, labeled immunoassays such as those from the group comprising radiolabeled immunoassay, enzyme immunoassays, more preferably ELISA, chemiluminscence immunoassays, preferably electrochemiluminescence immunoassay, and immunofluorescence, preferably indirect immunofluorescence.

In a preferred embodiment, the medical device is selected from the group comprising a glass slide, preferably for microscopy, a biochip, a microtiter plate, a lateral flow device, a test strip, a membrane, preferably a line blot, a chromatography column and a bead, preferably a magnetic or fluorescent bead.

The present invention is based on the inventors' surprising finding that an autoantibody to DAGLA exists and may be detected in samples from a number of patients suffering from neurological conditions, but not in samples obtained from healthy subjects.

Furthermore, the present invention is based on the inventors' surprising finding that the novel neurological disease may be diagnosed by way of detection of an autoantibody to DAGLA. Without wishing to be bound to any theory, the presence of such autoantibodies suggests that the function of DAGLA and/or downstream effectors is impaired in patients having such autoantibodies to the effect that neurological symptoms occur.

DAGLA (diacylglycerol lipase alpha, 120 kDa, 1.042 amino acids) is, together with DAGL-beta, a member of the DAG lipase (DAGL) family.

DAGLs are responsible for catalyzing the hydrolysis of diacylglycerol (DAG), one of the most studied second messenger in cells, to 2-arachidonoyl-glycerol (2-AG), the most abundant ligand for the endocannabinoid receptors (eCB) in the body (Keimpema, E. et al. (2013) Diacylglycerol lipase α manipulation reveals developmental roles for intercellular endocannabinoid signaling. Sci Rep. 3:2093/doi: 10.1038/srep02093). DAGL-dependent eCB signalling regulates axonal growth and guidance during development and is required for the generation and migration of new neurons in the adult brain (Williams, E. J. et al. (1994) The production of arachidonic acid can account for calcium channel activation in the second messenger pathway underlying neurite outgrowth stimulated by NCAM, N-cadherin, and L1. J. Neurochem. 62:1231-1234/doi:10.1046/j.1471-4159.1994.62/031,231.x). Beyond the encannabinoid system DAGLs influence the level of the essential lipid arachidonic acid via the synthesis of 2-AG in the brain and other organs (Reisenberg, M. et al. (2012) The diacylglycerol lipases: structure, regulation and roles in and beyond endocannabinoid signalling. Phil. Trans. R. Soc. B: 367, 3264-3275/doi:10.1098/rstb.2011.0387).

2-AG is mainly synthesized by DAGLA isoform whose expression correlates strongly with the total biosynthesis and release of 2-AG. The expression pattern of DAGLA changes from axonal tracts in the embryo to the dendritic fields and proliferating neural stem cells in the subventricular zone in the adult (Bisogno, T. et al. (2003) Cloning of the first sn1-DAG lipases points to the spatial and temporal regulation of endocannabinoid signaling in the brain. J Cell Biol. 163(3):463-8/doi/10.1083/jcb.200305129).

Genetic defects in DAGLA are potentially associated with the development of spinocerebellar ataxia type 20 (SCA20) in humans (Knight, M. A. et al. (2008) A duplication at chromosome 11q12.2-11q12.3 is associated with spinocerebellar ataxia type 20. Hum Mol Genet. 17(24):3847-3853. doi:10.1093/hmg/ddn283). Spinocerebellar ataxia is a clinically and genetically heterogeneous group of cerebellar disorders. Patients show progressive incoordination of gait and often poor coordination of hands, speech and eye movements, due to degeneration of the cerebellum with variable involvement of the brainstem and spinal cord (Knight, M. A. et al. (2004) Dominantly inherited ataxia and dysphonia with dentate calcification: spinocerebellar ataxia type 20. Brain. 127: 1172-1181/doi: 10.1093/brain/awh139).

DAGLA consists of a short cytoplasmic N-terminal sequence leading to a 4 transmembrane (4TM) helix domain, followed by a canonical alpha/beta hydrolase domain that harbors the catalytic domain, followed by a long C-terminal tail domain. The 4TM domain is conserved in the 19 AA N-terminal sequence. The 4TMs are separated by short unconcerned loops and two extracellular transmembrane domains represent potential sites for glycosylation.

Functionally, it is assumed that DAGLA facilitates the packing of enzymes at the membrane and acts as docking sites for other proteins in a functional complex and forms a channel that regulates DAG access to the catalytic domain and release of 2-AG from cells afterwards. The catalytic domain consists of in total 8 mutually hydrogen-bonded beta-sheet strands linked mostly by alpha-helices. Characteristically, it has a catalytic serine (AA 472) and aspartic acid (AA 524) and histidine (AA 650), the so called catalytic triad (Baggelaar, M. P. et al. (2013) Development of an Activity-Based Probe and In Silico Design Reveal Highly Selective Inhibitors for Diacylglycerol Lipase-alpha in Brain. Angw. Chem. Int. Ed. 52:1-6/doi:10.1002/anie.201306295). The catalytic action of DAGLA requires Ca2+ as an essential cofactor. Further, the catalytic domain includes a regulatory loop (appr. 50-60 AA long, between 7th and 8th canonical beta-sheet), which harbors a conserved 10 AA poly-proline signature motif (PLYPPGRIIH). This might function as cap or lid to shield hydrophobic catalytic cavity from water (Miled, N. et al. (2003) Importance of the lid and cap domains for the catalytic activity of gastric lipases. Comp Biochem Physiol B Biochem Mol Biol. 136(1): 131-8/doi: 10.1016/S 1096-4959(03)00183-0). The C-terminus of DAGLA is the most characteristic structural difference between the alpha and beta isoform. DAGLA but not DAGL-beta shows a long intracellular sequence. This DAGLA specific tail does not directly contribute to catalytic activity. Though, the integrated consensus motif (PPxxF) has been shown to bind the coiled-coil domain of Homer proteins (e.g. in mGluR interaction).

The present invention relates to a polypeptide comprising a mammalian, preferably human polypeptide selected from DAGLA or antigenic variants reactive to autoantibodies binding to DAGLA. Mammalian DAGLA includes homologues from human, monkey, mouse, rat, rabbit, guinea pig or pig, preferably human.

In a more preferred embodiment, DAGLA is the polypeptide encoded by SEQ ID NO4, Q9Y4D2 (alpha) (identical to SEQ ID NO4), NP_631918.3 (beta isoform 1) NP_001136408.1 (beta isoform 2), preferably Q9Y4D2. The cDNA consisting of the nucleic acid encoding SEQ ID NO4 is SEQ ID NO1. Throughout this application, any data base codes cited refers to the Uniprot data base, more specifically the version on the filing date of this application or its earliest priority application.

The teachings of the present invention may not only be carried out using polypeptides, in particular a polypeptide comprising the native sequence of a polypeptide such as DAGLA or nucleic acids having the exact sequences referred to in this application explicitly, for example by function, name, sequence or accession number, or implicitly, but also using variants of such polypeptides or nucleic acids.

In a preferred embodiment, the term "variant", as used herein, may refer to at least one fragment of the full length sequence referred to, more specifically one or more amino acid or nucleic acid sequence which is, relative to the full-length sequence, truncated at one or both termini by one or more amino acids. Such a fragment comprises or encodes for a peptide having at least 6, 7, 8, 10, 12, 15, 20, 25, 50, 75, 100, 150 or 200 successive amino acids of the original sequence or a variant thereof. The total length of the variant may be at least 6, 7, 8, 9, 10, 11, 12, 20, 25, 30, 40, 50, 60, 70, 80, 90, 100, 200, 300, 400, 500, 750, 1000 or more amino acids.

The term "variant" relates not only to at least one fragment, but also to a polypeptide or a fragment thereof comprising amino acid sequences that are at least 40, 50, 60, 70, 75, 80, 85, 90, 92, 94, 95, 96, 97, 98 or 99% identical to the reference amino acid sequence referred to or the fragment thereof, wherein amino acids other than those essential for the biological activity, for example the ability of an antigen to bind to an (auto)antibody, or the fold or structure of the polypeptide are deleted or substituted and/or one or more such essential amino acids are replaced in a conservative manner and/or amino acids are added such that the biological activity of the polypeptide is preserved. The state of the art comprises various methods that may be used to align two given nucleic acid or amino acid sequences and to calculate the degree of identity, see for example Arthur Lesk (2008), Introduction to bioinformatics, Oxford University Press, 2008, 3$^{rd}$ edition. In a preferred embodiment, the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007). Clustal W and Clustal X version 2.0. Bioinformatics, 23, 2947-2948) is used using default settings. Preferred variants or fragments having such biological activity are SEQ ID NO26 and SEQ ID NO28 and the His-tagged versions of them.

In a preferred embodiment, the variant is a linear, non-folded polypeptide, which is optionally denatured.

In a preferred embodiment, the polypeptide and variants thereof may, in addition, comprise chemical modifications, for example isotopic labels or covalent modifications such as glycosylation, phosphorylation, acetylation, decarboxylation, citrullination, methylation, hydroxylation and the like. The person skilled in the art is familiar with methods to modify polypeptides. Any modification is designed such that it does not abolish the biological activity of the variant.

Moreover, variants may also be generated by fusion with other known polypeptides or variants thereof and comprise active portions or domains, preferably having a sequence identity of at least 70, 75, 80, 85, 90, 92, 94, 95, 96, 97, 98 or 99% when aligned with the active portion of the reference sequence, wherein the term "active portion", as used herein, refers to an amino acid sequence, which is less than the full length amino acid sequence or, in the case of a nucleic acid sequence, codes for less than the full length amino acid sequence, respectively, and/or is a variant of the natural sequence, but retains at least some of the biological activity.

In a preferred embodiment, the term "variant" of a nucleic acid comprises nucleic acids the complementary strand of which hybridizes, preferably under stringent conditions, to the reference or wild type nucleic acid. Stringency of hybridization reactions is readily determinable by one of ordinary skilled in the art, and in general is an empirical calculation dependent on probe length, washing temperature and salt concentration. In general longer probes require higher temperatures for proper annealing, while shorter probes less so. Hybridization generally depends on the ability of denatured DNA to reanneal to complementary strands present in an environment below their melting temperature: The higher the degree of desired homology between the probe and hybridizable sequence, the higher the relative temperature which may be used. As a result, higher relative temperatures would tend to make the reaction conditions more stringent, while lower temperature less so. For additional details and explanation of stringency of hybridization reactions, see Ausubel, F. M. (1995), Current Protocols in Molecular Biology. John Wiley & Sons, Inc. Moreover, the person skilled in the art may follow the instructions given in the manual Boehringer Mannheim GmbH (1993) The DIG System Users Guide for Filter Hybridization, Boehringer Mannheim GmbH, Mannheim, Germany and in Liebl, W., Ehrmann, M., Ludwig, W., and Schleifer, K. H. (1991) International Journal of Systematic Bacteriology 41: 255-260 on how to identify DNA sequences by means of hybridization. In a preferred embodiment, stringent conditions are applied for any hybridization, i.e. hybridization occurs only if the probe is 70% or more identical to the target sequence. Probes having a lower degree of identity with respect to the target sequence may hybridize, but such hybrids are unstable and will be removed in a washing step under stringent conditions, for example lowering the concentration of salt to 2×SSC or, optionally and subsequently, to 0,5×SSC, while the temperature is, in order of increasing preference, approximately 50° C.-68° C., approximately 52° C.-68° C., approximately 54° C.-68° C., approximately 56° C.-68° C., approximately 58° C.-68° C., approximately 60° C.-68° C., approximately 62° C.-68° C., approximately 64° C.-68° C., approximately 66° C.-68° C. In a particularly preferred embodiment, the temperature is approximately 64° C.-68° C. or approximately 66° C.-68° C. It is possible to adjust the concentration of salt to 0.2×SSC or even 0.1×SSC. Nucleic acid sequences having a degree of identity with respect to the reference or wild type sequence of at least 70, 80, 90, 91, 92, 93, 94, 95, 96, 97, 98, 99% may be isolated. In a preferred embodiment, the term variant of a nucleic acid sequence, as used herein, refers to any nucleic acid sequence that encodes the same amino acid sequence and variants thereof as the reference nucleic acid sequence, in line with the degeneracy of the genetic code.

The variant of the polypeptide has biological activity. In a preferred embodiment, such biological activity is the ability to bind specifically to an autoantibody binding to DAGLA, as found in a patient suffering from an autoimmune disease associated with such autoantibody, preferably associated with a neurological disease or condition such as PNS. For example, whether or not a variant of DAGLA has such biological activity may be checked by determining whether or not the variant of interest binds to an autoantibody from a sample of a patient which autoantibody binds to wild type DAGLA, preferably as determined by indirect immunofluorescence using primate cerebellum as described in the experimental section of this application.

Any polypeptide according to the present invention, when used to carry out the teachings of the present invention, may be provided in any form and at any degree of purification, from liquid samples, tissues or cells comprising said polypeptide in an endogenous form, more preferably cells overexpressing the polypeptide, crude or enriched lysates of such cells, to purified and/or isolated polypeptide which is optionally essentially pure. In a preferred embodiment, the polypeptide is a native polypeptide, wherein the term "native polypeptide", as used herein, refers to a folded polypeptide, more preferably to a folded polypeptide purified from tissues or cells, more preferably from mammalian cells or tissues, optionally from non-recombinant tissues or cells. In another preferred embodiment, the polypeptide is a recombinant protein, wherein the term "recombinant", as used herein, refers to a polypeptide produced using genetic engineering approaches at any stage of the production process, for example by fusing a nucleic acid encoding the polypeptide to a strong promoter for overexpression in cells or tissues or by engineering the sequence of the polypeptide itself. The person skilled in the art is familiar with methods for engineering nucleic acids and polypeptides encoded (for example, described in Sambrook, J., Fritsch, E. F. and Maniatis, T. (1989), Molecular Cloning, CSH or in Brown T. A. (1986), Gene Cloning—an introduction, Chapman & Hall) and for producing and purifying native or recombinant polypeptides (for example Handbooks "Strategies for Protein Purification", "Antibody Purification", "Purifying Challenging Proteins" (2009/2010), published by GE Healthcare Life Sciences, and in Burgess, R. R., Deutscher, M. P. (2009), Guide to Protein Purification). In a preferred embodiment, a polypeptide is pure if at least 60, 70, 80, 90, 95 or 99 percent of the polypeptide in the respective sample consists of said polypeptide as judged by SDS polyacrylamide gel electrophoresis followed by Coomassie blue staining and visual inspection.

If the inventive polypeptide is provided in the form of tissue, it is preferred that the tissue is mammalian tissue, for example human, rat, primate, donkey, mouse, goat, horse, sheep, pig or cow, more preferably brain tissue, most preferably cerebellum. If a cell lysate is used, it is preferred that the cell lysate comprises the membranes associated with the surface of the cell or is in fact a fraction enriched in membranes. If said polypeptide is provided in the form of a recombinant cell, it is preferred that the recombinant cell is a eukaryotic cell such as a yeast cell, more preferably a cell from a multicellular eukaryote such as a plant, mammal, frog or insect, most preferably from a mammal, for example rat, human, primate, donkey, mouse, goat, horse, sheep, pig or cow.

The polypeptide used to carry out the inventive teachings, including any variants, is preferably designed such that it comprises at least one epitope recognized by and/or binds specifically to the autoantibody binding to DAGLA. Any epitope is more preferably an epitope recognized by such an autoantibody only, by contrast to antibodies other than an autoantibody to DAGLA. In one embodiment, such polypeptide comprises a stretch of 6, 7, 8, 9, 10, 11, 12, 20, 25, 30, 40, 50, 60, 70, 80, 90, 100 or more, preferably at least 9 but no more than 16, consecutive amino acids from DAGLA. The person skilled in the art is familiar with guidelines used to design peptides having sufficient immunogenicity, for example those described in Jackson, D. C., Fitzmaurice, C. J., Brown, L. E., Zeng, W. (1999), Preparation and properties of totally synthetic immunogens, Vaccine Volume 18, Issues 3-4, September 1999, Pages 355-361; and Black, M., Trent, A., Tirrell, M. and Olive, C. (2010), Advances in the design and delivery of peptide subunit vaccines with a focus on Toll-like receptor agonists, Expert Rev Vaccines, 2010 Feb.; 9(2): 157-173. Briefly, it is desirable that the peptide meets as many as possible of the following requirements: (a) it has a high degree of hydrophilicity, (b) it comprises one or more residues selected from the group comprising aspartate, proline, tyrosine and phenylalanine, (c) is has, for higher specificity, no or little homology with other known peptides or polypeptides, (d) it needs to be sufficiently soluble and (e) it comprises no glycosylation or phosphorylation sites unless required for specific reasons. Alternatively, bioinformatics approaches may be followed, for example those described by Moreau, V., Fleury, C., Piquer, D., Nguyen, C., Novali, N., Villard, S., Laune, D., Granier, C. and Molina, F. (2008), PEPOP: Computational design of immunogenic peptides, BMC Bioinformatics 2008, 9:71. Suitable epitopes are present in SEQ ID NO 16 and SEQ ID NO 22.

The inventive polypeptide, when used according to the present invention, may be provided in any kind of conformation. For example, the polypeptide may be an essentially unfolded, a partially or a fully folded polypeptide. In a preferred embodiment, the polypeptide is folded in the sense that the epitopes essential for the binding to the inventive autoantibody, or the protein or variant thereof in its entirety, adopt the fold adopted by the native protein in its natural environment. The person skilled in the art is familiar with methods suitable to determine whether or not a polypeptide is folded and if it is, which structure it has, for example limited proteolysis, NMR spectroscopy, CD spectroscopy or X-ray crystallography (see for example Banaszak L. J. (2008), Foundations of Structural Biology, Academics Press, or Teng Q. (2013), Structural Biology: Practical Applications, Springer), preferably CD spectroscopy is used.

The inventive polypeptide may be a fusion protein which comprises amino acid sequences other than those taken from DAGLA, in particular a C-terminal or N-terminal tag, preferably a C-terminal tag, which is, in a preferred embodiment, as used herein, an additional sequence motif or polypeptide having a function that has some biological or physical function and may, for example, be used to purify, immobilize, precipitate or identify the inventive polypeptide. In a more preferred embodiment, the tag is a sequence or domain capable of binding specifically to a ligand, for example a tag selected from the group comprising His tags, thioredoxin, maltose binding protein, glutathione-S-transferase, a fluorescence tag, for example from the group comprising green fluorescent protein.

The inventive polypeptide may be an immobilized polypeptide. In a preferred embodiment, the term "immobilized", as used herein, refers to a molecule bound to a solid carrier insoluble in an aqueous solution, more preferably via a covalent bond, electrostatic interactions, encapsulation or entrapment, for example by denaturing a globular polypeptide in a gel, or via hydrophobic interactions, most preferably via one or more covalent bonds. Various suitable carriers, for example paper, polystyrene, metal, silicon or glass surfaces, microfluidic channels, membranes, beads such as magnetic beads, column chromatography media, biochips, polyacrylamide gels and the like have been described in the literature, for example in Kim, D., and Herr, A. E. (2013), Protein immobilization techniques for microfluidic assays, Biomicrofluidics 7(4), 041501. This way, the immobilized molecule, together with the insoluble carrier, may be separated from an aqueous solution in a straightforward manner, for example by filtration, centrifugation or decanting. An immobilized molecule may be immobilized in a reversible or irreversible manner. For example, the immobilization is reversible if the molecule interacts with the carrier via ionic interactions that can be masked by addition of a high concentration of salt or if the molecule is bound via a cleavable covalent bond such as a disulphide bridge which may be cleaved by addition of thiol-containing reagents. By contrast, the immobilization is irreversible if the molecule is tethered to the carrier via a covalent bond that cannot be cleaved in aqueous solution, for example a bond formed by reaction of an epoxide group and an amine group as frequently used to couple lysine side chains to affinity columns. The protein may be indirectly immobilized, for example by immobilizing an antibody or other entity having affinity to the molecule, followed by formation of a complex to the effect that the molecule-antibody complex is immobilized. Various ways to immobilize molecules are described in the literature, for example in Kim, D., Herr, and A. E. (2013), Protein immobilizsation techniques for microfluidic assays, Biomicrofluidics 7(4), 041501. In addition, various reagents and kits for immobilization reactions are commercially available, for example from Pierce Biotechnology.

It is essential that the sample used for the diagnosis in line with the detection of autoantibodies according to the present invention comprises antibodies, also referred to as immunoglobulins. Typically the sample of a bodily fluid comprises a representative set of the entirety of the subject's immunoglobulins. However, the sample, once provided, may be subjected to further processing which may include fractionation, centrifugation, enriching or isolating the entirety of immunoglobulins or any immunoglobulin class of the subject, which may affect the relative distribution of immunoglobulins of the various classes.

The reagents, devices, methods and uses described throughout this application may be used for the diagnosis of a disease. In a preferred embodiment, the disease is a neurological disease. In a more preferred embodiment, the term "neurological disease", as used herein, refers to any disease associated with a defect of the nervous system, in another preferred embodiment, the term "PNS", abbreviation of paraneoplastic neurological syndrome, as used herein, refers to a systemic disorder indirectly caused by the presence of a tumor, for example, as a result of the production release of substances such as hormones or cytokines not normally produced by the cell of origin of the tumor or are produced at increased concentration or the production and release of biologically active cells. Such systemic order may be revealed by various conditions comprising cerebellitis, epilepsy and sclerosis. Any manifestation of PNS indicates that the patient should be thoroughly examined for the presence of a tumor, although the tumor may be too small for detection.

Cerebellitis can have a variety of causes and be related to the following diseases, which may therefore be diagnosed or distinguished or differentiated from autoimmune cerebellitis using the present invention: Virus infection, for example with Coxsackie, Influenza, Varicella Zoster, Eppstein-Barr, Rotavirus or Parvovirus, bacterial infection, for example *Mycobacterium pneumoniae* or *Cryptococcus*, ataxia, autoimmune cerebellitis, for example associated with autoantibodies to Neurochrondrin or Yo, drug overdose, for example by methadone or opium, vaccine-induced cerebellitis.

Epilepsy can have a variety of causes and be related to the following diseases, which may therefore be diagnosed or distinguished or differentiated from autoimmune cerebellitis using the present invention: benign febrile convulsions of childhood, idiopathic/cryptogenic seizures, cerebral dysgenesis, symptomatic epilepsy, head trauma, stroke, vascular malformations, mass lesions, CNS infections, encephalitis, ceningitis, cysticercosis, HIV encephalopathy, hypoglycemia, hyponatremia, hyperosmolar states, hypocalcemia, uremia, hepatic encephalopathy, porphyria, drug toxicity, drug withdrawal, global cerebral ischemia, hypertensive encephalopathy, eclampsia, hyperthermia.

Sclerosis can have a variety of causes and be related to the following diseases, which may therefore be diagnosed or distinguished or differentiated from autoimmune cerebellitis using the present invention: Lou Gehrig's disease, Atherosclerosis, nephrotic syndrome, Hippocampal sclerosis, Lichen sclerosus and Multiple sclerosis.

Therefore, the present invention may also be used for distinguishing an autoimmune disease from an infectious disease, in particular a neuronal autoimmune disease from an infectious disease. Detection of the autoantibody to DAGLA shows that the disease is an autoimmune disease.

In a preferred embodiment, the term "diagnosis", as used herein, refers to any kind of procedure aiming to obtain information instrumental in the assessment whether a patient suffers or is likely or more likely than the average or a comparative subject, the latter preferably having similar symptoms, to suffer from certain a disease or disorder in the past, at the time of the diagnosis or in the future, to find out how the disease is progressing or is likely to progress in the future or to evaluate the responsiveness of a patient with regard to a certain treatment, for example the administration of immunosuppressive drugs. In other words, the term "diagnosis" comprises not only diagnosing, but also prognosticating and/or monitoring the course of a disease or disorder. In many cases the mere detection, in other words determining whether or not detectable levels of the antibody are present in the sample, is sufficient for the diagnosis. If the autoantibody can be detected, this will be information instrumental for the clinician's diagnosis and indicates an increased likelihood that the patient suffers from a disease. In a preferred embodiment, the autoantibody is deemed detectable if it can be detected using one or more methods selected from the group comprising immunoprecipitation, indirect immunofluorescence, ELISA or line blot, preferably indirect immunofluorescence. In a preferred embodiment, the relative concentration of the antibody in the serum, compared to the level that may be found in the average healthy subject, may be determined. While in many cases it may be sufficient to determine whether or not autoantibodies are present or detectable in the sample, the method carried out to obtain information instrumental for the diagnosis may involve determining whether the concentration is at least 2, preferably 5, 10, 20, 25, 50, 100, 200, 500, 1000, 10000 or 100000 times higher than the concentration found in the average healthy subject. In a preferred embodiment, the relative concentration of the autoantibody is determined using one or more methods selected from the group comprising semi-quantitative immunoprecipitation, semi-quantitative indirect immunofluorescence, ELISA or semi-quantitative line blot, preferably ELISA. Experimental details are as described in the experimental section of this application or as in text books or practical manuals as available at the priority date of this application. Many assays may be carried out in a competitive format, wherein DAGLA or a variant thereof is bound to a first antibody, which is replaced by a second antibody. For example, the first antibody may be the autoantibody to DAGLA and the second antibody may be a recombinant antibody, preferably labeled with a detectable label.

The person skilled in the art will appreciate that a clinician does usually not conclude whether or not the patient suffers or is likely to suffer from a disease, condition or disorders solely on the basis of a single diagnostic parameter, but needs to take into account other aspects, for example the presence of other autoantibodies, markers, blood parameters, clinical assessment of the patient's symptoms or the results of medical imaging or other non-invasive methods such as polysomnography, to arrive at a conclusive diagnosis. See Baenkler H. W. (2012), General aspects of autoimmune diagnostics, in Renz, H., Autoimmune diagnostics, 2012, de Gruyter, page 3. The value of a diagnostic agent or method may also reside the possibility to rule out one disease, thus allowing for the indirect diagnosis of another. In a preferred embodiment, the meaning of any symptoms or diseases referred to throughout this application is in line with the person skilled in the art's understanding as of the filing date or, preferably, earliest priority date of this application as evidenced by text books and scientific publications. It should be mentioned that the inventive methods or uses or products, taken alone, cannot be used to arrive at a definite, final diagnosis.

Therefore, the term "diagnosis" does preferably not imply that the diagnostic methods or agents according to the present invention will be definitive and sufficient to finalize the diagnosis on the basis of a single test, let alone parameter, but may refer to a contribution to what is referred to as a "differential diagnosis", i. e. a systematic diagnostic procedure considering the likelihood of a range of possible conditions on the basis of a range of diagnostic parameters. Consequently, the inventive method, polypeptide or use, optionally for determining whether a patient suffers from the a disease, may comprise obtaining a sample from a patient, preferably a human patient, determining whether an autoantibody binding to DAGLA is present in said sample, wherein said determining is performed by contacting the sample with the inventive polypeptide and detecting whether binding occurs between said polypeptide and said autoantibody, preferably using a labeled secondary antibody, wherein said autoantibody binds to said polypeptide if present in the sample, and diagnosing the patient as suffering or being more likely to suffer from said neurological disorder if the autoantibody was determined to be present in the sample.

The term "diagnosis" may also refer to a method or agent used to distinguish between two or more conditions associated with similar or identical symptoms.

The term "diagnosis" may also refer to a method or agent used to choose the most promising treatment regime for a patient. In other words, the method or agent may relate to selecting a treatment regimen for a subject. For example, the detection of autoantibodies may indicate that an immunosuppressive therapy is to be selected, which may include administrating to the patient one or more immunosuppressive drugs.

The present invention relates to a complex comprising an antibody, preferably autoantibody, binding to the inventive polypeptide. Such a complex may be used or detected as part of a method for diagnosing a disease. A liquid sample comprising antibodies from a subject may be used to practice the method if an autoantibody to DAGLA is to be detected. Such a liquid sample may be any bodily fluid comprising a representative set of antibodies from the subject, preferably a sample comprising antibodies of an immunoglobulin class from the subject selected from the group comprising IgG, IgA and IgM class antibodies, preferably IgG, more preferably IgG1 and IgG2, more preferably IgG1. For example, a sample may be cerebrospinal fluid (CSF), blood or blood serum, lymph, insterstitial fluid and is preferably serum or CSF, more preferably serum. It is preferably an ex vivo sample.

The step contacting a liquid sample comprising antibodies with the inventive polypeptide(s) may be carried out by incubating an immobilized form of said polypeptide(s) in the presence of the sample comprising antibodies under conditions that are compatible with the formation of the complex comprising the respective polypeptide and an antibody, preferably an autoantibody, binding to the inventive polypeptide. The liquid sample, then depleted of antibodies binding to the inventive polypeptide(s) may be removed subsequently, followed by one or more washing steps. Finally the complex comprising the antibody or antibodies and the polypeptide(s) may be detected. In a preferred embodiment, the term "conditions compatible with the formation of the complex" are conditions that allow for the specific antigen-antibody interactions to build up the complex comprising the polypeptide and the antibody. In a preferred embodiment such conditions may comprise incubating the polypeptide in sample diluted 1:100 in PBS buffer for 30 minutes at 25° C.

In a preferred embodiment, the term "autoantibody", as used herein, refers to an antibody binding specifically to an endogenous molecule of the animal, preferably mammal, more preferably human, which produces said autoantibody, wherein the level of such antibody is more preferably elevated compared the average of any other antibodies binding specifically to such an endogenous molecule. In a most preferred embodiment, the autoantibody is an autoantibody binding to DAGLA. The autoantibody may have the sequence of an antibody's constant regions from the animal, preferably human, making it, but the variable region is able to bind specifically to the endogenous molecule of the animal, more specifically DAGLA. In a preferred embodiment, the autoantibody is isolated and/or purified from a sample, preferably tissue, serum, plasma, blood or CSF from the animal, preferably human. The autoantibody is a polyclonal, native antibody from the animal rather than a synthetic or recombinant antibody. In a preferred embodiment, the autoantibody is an antibody binding specifically to SEQ ID NO 26 or SEQ ID NO 28, preferably SEQ ID NO28.

The method according to the present invention is preferably an in vitro method.

In a preferred embodiment, the detection of the complex for the prognosis, diagnosis, methods or test kit according to the present invention comprises the use of a method selected from the group comprising immunodiffusion techniques, immunoelectrophoretic techniques, light scattering immunoassays, agglutination techniques, labeled immunoassays such as those from the group comprising radiolabeled immunoassay, enzyme immunoassays, preferably ELISA, chemiluminscence immunoassays, and immunofluorescence, preferably indirect immune-fluorescence techniques. The person skilled in the art is familiar with these methods, which are also described in the state of the art, for example in Zane, H. D. (2001), Immunology—Theo-retical & Practical Concepts in Laboratory Medicine, W. B. Saunders Company, in Chapter 14.

Alternatively, a sample comprising tissue comprising the inventive polypeptide rather than a liquid sample may be used. The tissue sample is preferably from a tissue expressing endogenous DAGLA, preferably at an increased level compared to the average tissue in the respective organism's, preferably human body. Such a sample, which may be in the form of a tissue section fixed on a carrier, for example a glass slide for microscopic analysis, may then be contacted with the inventive antibody, preferably autoantibody, binding to the inventive polypeptide. The antibody is preferably labeled to allow for distinction from endogenous antibodies binding to the inventive polypeptide, so that newly formed complexes may be detected and, optionally, quantified. If the amount of complexes formed is lower than the amount found in a sample taken from a healthy subject, the subject from whom the sample examined has been taken is likely to suffer from a disease.

Any data demonstrating the presence or absence of the complex comprising the antibody and the inventive polypeptide may be correlated with reference data. For example, detection of said complex indicates that the patient who provided the sample analyzed has suffered, is suffering or is likely to suffer in the future from a disease. If a patient has been previously diagnosed and the method for obtaining diagnostically relevant information is run again, the amount of complex detected in both runs may be correlated to find out about the progression of the disease and/or the success of a treatment. In a preferred embodiment, any information or data demonstrating the presence of absence of the complex may be communicated to the patient or a medical doctor treating the patient, preferably by telephone, in a written form or via the internet, for example as an email or text message.

In another preferred embodiment, the prognosis, diagnosis, methods or test kit in line with the inventive teachings contemplate the use of indirect immunofluorescence. The person skilled in the art is familiar with such techniques and the preparation of suitable samples, which are described in the state of the art (U.S. Pat. No. 4,647,543; Voigt, J., Krause, C., Rohwader, E, Saschenbrecker, S., Hahn, M., Danckwardt, M., Feirer, C., Ens, K, Fechner, K, Barth, E, Martinetz, T., and Stöcker, W. (2012), Automated Indirect Immunofluorescence Evaluation of Antinuclear Autoantibodies on HEp-2 Cells," Clinical and Developmental Immunology, vol. 2012, doi:10.1155/2012/65105; Bonilla, E., Francis, L., Allam, F., et al., Immuno-fluorescence microscopy is superior to fluorescent beads for detection of antinuclear antibody reactivity in systemic lupus erythematosus patients, Clinical Immunology, vol. 124, no. 1, pp. 18-21, 2007). Suitable reagents, devices and software packages are commercially available, for example from EUROIMMUN, Lübeck, Germany.

A sample may be subjected to a test to determine only whether an autoantibody binding to DAGLA is present, but it is preferred that diagnostic methods, tests, devices and the like contemplate determining the presence of autoantibodies to one or more additional polypeptides, preferably related to neurological autoimmune diseases, preferably selected from, more preferably all from the group comprising Hu, Yo, Ri, CV2, PNMA1, PNMA2, DNER/Tr, ARHGAP26, ITPR1, ATP1A3, NBC1, Neurochrondrin, CARPVIII, Zic4, Sox1, Ma, MAG, MP0, MBP, GAD65, amphiphysin, recoverin, GABA A receptor (EP13189172.3), GABA B receptor (EP2483417), glycine receptor, gephyrin, IgLON5 (US2016/0349275), DPPX (US2015/0247847), aquaporin-4, MOG, NMDA receptor, AMPA receptors, GRM1, GRM5, LGI1, VGCC und mGluR1 and CASPR2, which antigens are preferably immobilized, for example on a medical device such as a line blot. The diagnostically relevant markers Neurochrondrin (EP15001186), ITPR1 (EP14003703.7), NBC1 (EP14003958.7), ATP1A3, also referred to as alpha 3 subunit of human neuronal Na(+)/K(+) ATPase (EP14171561.5), Flotillin1/2 (EP3101424), NSF, STX1B and VAMP2 (EP17001205.8) and RGS8 (EP17000666.2), autoantibodies to one or more of which, preferably all, may be detected in addition, have been described in the state of the art.

According to the teachings of the present invention, an antibody, preferably an autoantibody binding to the inventive polypeptide used for the diagnosis of a disease is provided. The person skilled in the art is familiar with methods for purifying antibodies, for example those described in Hermanson, G. T., Mallia, A. K., and Smith, P. K. (1992), Immobilized Affinity Ligand Techniques, San Diego: Academic Press. Briefly, an antigen binding specifically to the antibody of interest, which antigen is the inventive polypeptide, is immobilized and used to purify, via affinity chromatography, the antibody of interest from an adequate source. A liquid sample comprising antibodies from a patient suffering from the neurological disorder identified by the inventors may be used as the source.

According to the invention, an antibody, for example an autoantibody, is provided that is capable of binding specifically to DAGLA. Vice versa, a variant of DAGLA binds specifically to an autoantibody binding specifically to DAGLA. In a preferred embodiment, the term "antibody", as used herein, refers to any immunoglobulin-based binding moieties, more preferably one comprising at least one immunoglobulin heavy chain and one immunoglobulin light chain, including, but not limited to monoclonal and polyclonal antibodies as well as variants of an antibody, in particular fragments, which binding moieties are capable of binding to the respective antigen, more preferably binding specifically to it. In a preferred embodiment, the term "binding specifically", as used herein, means that the binding is stronger than a binding reaction characterized by a dissociation constant of $1 \times 10^{-5}$ M, more preferably $1 \times 10^{-7}$ M, more preferably $1 \times 10^{-8}$ M, more preferably $1 \times 10^{-9}$ M, more preferably $1 \times 10^{-10}$ M, more preferably $1 \times 10^{-11}$ M, more preferably $1 \times 10^{-12}$ M, as determined by surface plasmon resonance using Biacore equipment at 25° C. in PBS buffer at pH 7. The antibody may be part of an autoantibody preparation which is heterogeneous or may be a homogenous autoantibody, wherein a heterogeneous preparation comprises a plurality of different autoantibody species as obtainable by preparation from the sera of human donors, for example by affinity chromatography using the immobilized antigen to purify any autoantibody capable of binding to said antigen. The antibody may be glycosylated or non-glycosylated. The antibody may be a recombinant and/or monoclonal mammalian antibody, preferably an animal which is not a human. The antibody may be an antibody binding specifically against SEQ ID NO 26 or SEQ ID NO 28, preferably SEQ ID NO28. The person skilled in the art is familiar with methods that may be used for the identification, production and purification of antibodies and variants thereof, for examples those described in EP 2 423 226 A2 and references therein. Preferably the antibody is purified and/or recombinant. Preferably the antibody is bound to the diagnostically useful carrier.

The present invention provides a method for isolating an autoantibody binding to DAGLA, comprising the steps a) contacting a sample comprising the antibody with the inventive polypeptide such that a complex is formed, b) isolating the complex formed in step a), c) dissociating the complex isolated in step b), and d) separating the antibody from the inventive polypeptide. A sample from a patient suffering from the novel neurological disorder identified by the inventors may be used as the source of antibody. Suitable methods are described in the state of the art, for example in the Handbooks "Affinity chromatography", "Strategies for Protein Purification" and "Antibody Purification" (2009/2010), published by GE Healthcare Life Sciences, and in Philips, Terry, M., Analytical techniques in immunochemistry, 1992, Marcel Dekker, Inc.

The invention provides a pharmaceutical composition comprising the inventive polypeptide, which composition is preferably suitable for administration to a subject, preferably a mammalian subject, more preferably to a human. Such a pharmaceutical composition may comprise a pharmaceutically acceptable carrier. The pharmaceutical composition may, for example, be administered orally, parenterally, by inhalation spray, topically, by eyedrops, rectally, nasally, buccally, vaginally or via an implanted reservoir, wherein the term "parentally", as used herein, comprises subcutaneous, intracutaneous, intravenous, intramuscular, intra-articular, intrasynovial, instrasternal, intrathecal, intralesional and intracranial injection or infusion techniques. The pharmaceutical composition may be provided in suitable dosage forms, for example capsules, tablets and aqueous suspensions and solutions, preferably in sterile form. It may be used in a method of treatment of a disease, which method comprises administering an effective amount of the inventive polypeptide to a subject. In a preferred embodiment, the invention provides a vaccine comprising the inventive polypeptide, optionally comprising an auxiliary agent such as an adjuvans or a buffer, and the use of the inventive polypeptide for the preparation of a vaccine.

Within the scope of the present invention, a medical or diagnostic device comprising, preferably coated with a reagent for detecting the inventive (auto)antibody and/or the inventive polypeptide is provided. Preferably such a medical or diagnostic device comprises the inventive polypeptide in a form that allows contacting it with an aqueous solution, more preferably the liquid human sample, in a straightforward manner. In particular, the inventive polypeptide comprising may be immobilized on the surface of a carrier, preferably selected from the group comprising glass plates or slides, biochips, microtiter plates, beads, for example magnetic beads, apharesis devices, chromatography columns, membranes or the like. Exemplary medical devices include line blots, microtiter plates, glass slides for microscopy, beads, preferably magnetic beads, and biochips. In addition to the inventive polypeptide, the medical or diagnostic device may comprise additional polypeptides, for example positive or negative controls such as samples comprising or not comprising an antibody binding to the polypeptide of interest, or known other antigens binding to autoantibodies of diagnostic value, particularly those related other diseases associated with one or more identical or similar symptoms.

The inventive teachings provide a kit, preferably for diagnosing a disease. Such a kit may comprise instructions detailing how to use the kit and a means for contacting the inventive polypeptide with a bodily fluid sample from a subject, preferably a human subject, for example a line blot, wherein the inventive polypeptide is immobilized on the line blot. Furthermore, the kit may comprise a positive control, for example a batch of autoantibody or recombinant antibody known to bind to the polypeptide according to the present invention, preferably against SEQ ID NO 26 and/or SEQ ID NO28, and a negative control, for example a protein having no detectable affinity to the inventive polypeptide such as bovine serum albumin. Finally, such a kit may comprise one or more standard solutions, also referred to as calibrator, of an antibody binding to DAGLA, preferably SEQ ID NO 26 and/or SEQ ID NO28, preferably with a known absolute or relative concentration, for preparing a calibration curve. Preferably the kit comprises two calibrators, wherein the first calibrator has a concentration of the antibody that is no more than 50, 40, 30, 20, 10 5, 2.5 or 1% of the concentration of the antibody in the second calibrator. In a preferred embodiment, a device comprising the diagnostically useful carrier is calibrated by detecting the antibody concentration in at least two calibrators and obtaining a concentration value for each calibrator, preferably three, four or five or more calibrators, followed by setting up a standard calibration curve.

In a preferred embodiment, the kit comprises a means for detecting an autoantibody binding to the inventive polypeptide, preferably by detecting a complex comprising the inventive polypeptide and an antibody binding to the inventive polypeptide. Such means is preferably an agent that binds to said complex and modifies the complex or carries a label such that makes the complex detectable. For example, said means may be a labeled antibody binding to said polypeptide, at a binding site other than the binding site recognized by the primary antibody or to a constant region of the primary antibody. Alternatively, said means may be a secondary antibody binding to the constant region of the autoantibody, preferably a secondary antibody specific for mammalian IgG class of antibodies. A multitude of methods and means for detecting such a complex have been described in the state of the art, for example in Philips, Terry, M., Analytical techniques in immunochemistry, 1992, Marcel Dekker, Inc.

DAGLA or a variant thereof may be produced or provided in the form of a cell comprising and/or expressing a nucleic acid encoding said polypeptide. If a nucleic acid comprising a sequence that encodes for the inventive polypeptide or variant thereof is used, such a nucleic acid may be an unmodified nucleic acid. In a preferred embodiment, the nucleic acid is a nucleic acid that, as such, does not occur in nature and comprises, compared to natural nucleic acid, at least one modification, for example an isotopic content or chemical modifications, for example a methylation, sequence modification, label or the like indicative of synthetic origin. In a preferred embodiment, the nucleic acid is a recombinant nucleic acid or part or a nucleic acid, and is, in a more preferred embodiment, part of a vector, in which it may be functionally linked with a promoter that allows for expression, preferably overexpression of the nucleic acid. The person skilled in the art is familiar with a variety of suitable vectors, of which are commercially available, for example from Origene. For example, a vector encoding for fusion constructs with a C-terminal GFP may be used. The cell may be a eukaryotic or prokaryotic cell, preferably of eukaryotic cell, such as a yeast cell, and is more preferably a mammalian, more preferably a human cell such as a HEK293 cell. Examples of a mammalian cell include a HEK293, CHO or COS-7 cell. The cell comprising the nucleic acid encoding for the inventive polypeptide may be a recombinant cell or an isolated cell wherein the term "isolated" means that the cell is enriched such that, compared to the environment of the wild type of said cell, fewer cells of other differentiation or species or in fact no such other cells are present. In a preferred embodiment, the vector encodes for a polypeptide comprising SEQ ID NO 26 and/or SEQ ID NO28, preferably SEQ ID NO28.

In a preferred embodiment, the medical device according to the present invention, preferably a slide suitable for microscopy, comprises one or more, preferably all reagents from the group comprising a first eukaryotic cell expressing, preferably overexpressing DAGLA or a variant thereof, a eukaryotic, preferably mammalian tissue expressing endogenous DAGLA such as rat or primate cerebellum, a second eukaryotic cell, which is the same type of cell as the first eukaryotic cell, but does not express or overexpress DAGLA. The first and the second eukaryotic cell are cultured cells derived from an isolated cell line such as HEK293. Preferably, the first and the second cell are each transfected with a vector sharing the same backbone, wherein the vector used to transfect the first cell comprises a nucleic acid encoding DAGLA or a variant thereof and the vector used to transfect the second cell does not comprise DAGLA or a variant thereof. The second cell may serve as a negative control. The reagents may be spatially separate on the medical device, such that they may be evaluated independently, with no antigen from one reagent contaminating another. In a more preferred embodiment, the first and/or the second cell is a fixed cell, for example fixed using methanol or acetone. Protocols for fixing cells are described in the state of the art. As an additional reagent, a secondary labeled antibody, preferably labeled with a fluorescent dye may be provided. The reagents and the medical device may be part of a kit.

In a preferred embodiment, a microtiter plate, membrane, blot such as dot blot or line blot is used to carry out the diagnostic method according to the invention. The person skilled in the art is familiar with the experimental setup of a line blot, which is described in the state of the art (Raoult, D., and Dasch, G. A. (1989), The line blot: an immunoassay for monoclonal and other antibodies. Its application to the serotyping of gram-negative bacteria. J. Immunol. Methods, 125 (1-2), 57-65; WO2013041540). If the medical device is a line blot, it may comprise DAGLA or a variant thereof immobilized on a membrane, preferably in the shape of a test stripe. The membrane may comprise one or more additional antigens, spatially separated from DAGLA. The membrane may comprise a control band indicating addition of the sample such as a blood sample and/or a control band indicating addition of a secondary antibody. A kit may comprise any component, preferably all from the group comprising the line blot, a secondary antibody and a washing solution.

In another preferred embodiment, the medical device is a microtiter plate comprising at least 8 wells. At least one of the wells is directly or indirectly coated with DAGLA or a variant thereof. At least 3, preferably 4, more preferably 5 calibrators are provided that comprise an antibody to DAGLA at a defined concentration and may be used to set up a calibration curve for semi-quantitative analysis. A secondary antibody comprising an enzymatically active label may be provided. A kit may comprise any component, preferably all from the group comprising the microtiter plate, the calibrators, a washing solution and the secondary antibody.

In another preferred embodiment, the medical device is a bead coated directly or indirectly with DAGLA or a variant thereof. The bead may be selected from the group comprising a magnetic bead and a fluorescent bead. A secondary antibody comprising a label capable or chemiluminescence or fluorescence may be provided. A positive control comprising an antibody to DAGLA may be provided. At least 3, preferably 4, more preferably 5 calibrators may be provided that comprise an antibody to DAGLA at a defined concentration and may be used to set up a calibration curve for semi-quantitative analysis. If the label is capable of generating chemiluminescence, a solution may be provided that comprises additional components required for the chemiluminscence reaction. For example, if the label is an enzyme, the solution comprises substrates. If the label is a compound capable of generating chemiluminescence such as an acridinium ester, additional compounds required for the reaction are provided in the solution. A kit may comprise any component, preferably all from the group comprising the bead, the secondary antibody, the calibrators, a washing solution and the solution comprising additional components.

The inventive teachings may not only be used for a diagnosis, but also for preventing or treating a disease, more specifically a method for preventing or treating a disease, comprising the steps a) reducing the concentration of autoantibodies binding to the inventive polypeptide in the subject's blood and/or b) administering one or more immunosuppressive pharmaceutical substances, preferably selected from the group comprising rituximab, prednisone, methylprednisolone, cyclophosphamide, mycophenolate-mofetil, intravenous immunoglobulin, tacrolimus, cyclosporine, methotrexate, azathioprine and/or the pharmaceutical composition.

In a preferred embodiment, the present invention provides a use of a reagent for the detection of an autoantibody to DAGLA or a reagent binding to such autoantibody, or of a nucleic acid encoding DAGLA or the variant or a nucleic acid hybridizing specifically to a nucleic acid encoding DAGLA or a vector or cell comprising said nucleic acid for the manufacture of kit for the diagnosis of a disease.

In a preferred embodiment, any method or use according to the present invention may be intended for a non-diagnostic use, i.e. determining the presence of an autoantibody to binding to DAGLA for a use other than diagnosing a patient. For example, the method or use may be for testing in vitro the efficiency of a medical device designed to remove an autoantibody from a patient's blood, wherein the testing is performed on a liquid other than patient's blood. After the use of the medical device with a patient, its capacity to remove autoantibody may be checked by running a solution comprising antibody to DAGLA through the device, followed by use of the method according to the present invention to confirm that less or no antibody is in the solution that has been passed through the device, i.e. showing that the device has still the capacity to remove antibody from the solution.

In another preferred embodiment, the method may be for confirming the reliability of a diagnostic assay and may involve detecting an antibody to DAGLA in a solution, which is not a sample from a patient, but is known to comprise an antibody to DAGLA, preferably at a known concentration. Alternatively, the solution may be a negative control not comprising the antibody to check the background. Such method may be run in parallel with, after or before a diagnostic method. In a preferred embodiment, any method or use according to the present invention may be intended for generating an autoantibody profile, preferably for detecting a disease in a mammal, preferably a human. In a preferred embodiment, any method or use may be for detecting disease-associated markers in a sample from neurological disease patients.

In a preferred embodiment, any method or use according to the present invention may be for identifying a subject at risk of suffering from or developing a neurological disease and/or a tumor.

In a preferred embodiment, the present invention provides an apparatus for analyzing a sample from a patient to detect an autoantibody against DAGLA, preferably SEQ ID NO 26 and/or SEQ ID NO 28, indicating an increased likelihood of a disease or of developing a disease, comprising:
  a. a carrier, which contains a means for capturing the autoantibody from the sample when the sample is contacted with the carrier,
  b. a detectable means capable of binding to the antibody captured by the carrier when the detectable means is contacted with the carrier, wherein the detectable means is a labeled secondary antibody capable of binding to the antibody captured on the carrier,
  c. optionally a means for removing any sample from the carrier and the detectable means, preferably by washing;
  d. a detecting device for detecting the presence of the detectable means and converting the results into an electrical signal, and
optionally a means for receiving the electronical signal from the detecting device and determining if the level of the signal is indicative of an increased likelihood of having or of developing a disease, by comparing with the level of signal detected in the background or an input reference value obtained with samples from healthy subjects or by comparing the level of signal obtained with one sample with the level of signal obtained with a second sample obtained at a later time point, preferably at least one month later.

FIG. 1 shows the results of indirect immunofluorescence assays of sera from patients P1 to P5 using permeabilized cryosections of rat and primate cerebellum. Granular staining of the molecular layer was observed.

Figure 2:
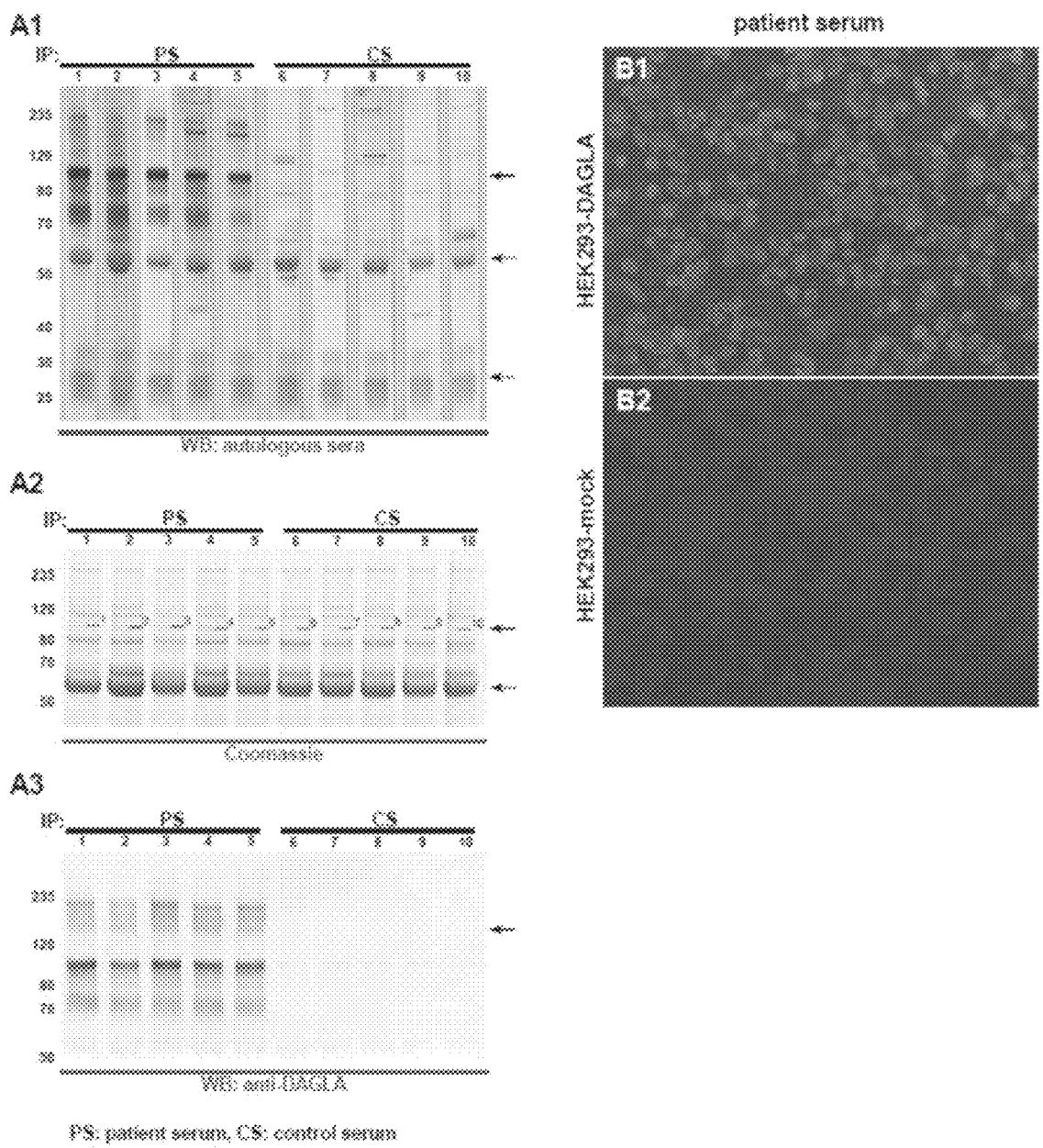
FIG. 2 shows immunoprecipitation of DAGLA from homogenized rat cerebellum using patient sera followed by Western Blot analysis using patient sera as antibody source (A1), Coomassie-stained SDS PAGE (A2), Western Blot using a commercial recombinant antibody binding to DAGLA (A3). Furthermore, the patients' samples were tested by indirect immunofluorescence using transfected HEK293 cells expressing DAGLA. Patients' sera reacted with the DAGLA-expressing cells (B1). In contrast, mock-transfected cell did not demonstrate any specific antibody binding (B2).

FIG. 2 shows immunoprecipitation of DAGLA from homogenized rat cerebellum using patient sera followed by Western Blot analysis using patient sera as antibody source (A1), Coomassie-stained SDS PAGE (A2), Western Blot using a commercial recombinant antibody binding to DAGLA (A3). Furthermore, the patients' samples were tested by indirect immunofluorescence using transfected HEK293 cells expressing DAGLA. Patients' sera reacted with the DAGLA-expressing cells (B1). In contrast, mock-transfected cell did not demonstrate any specific antibody binding (B2).

Figure 3A:
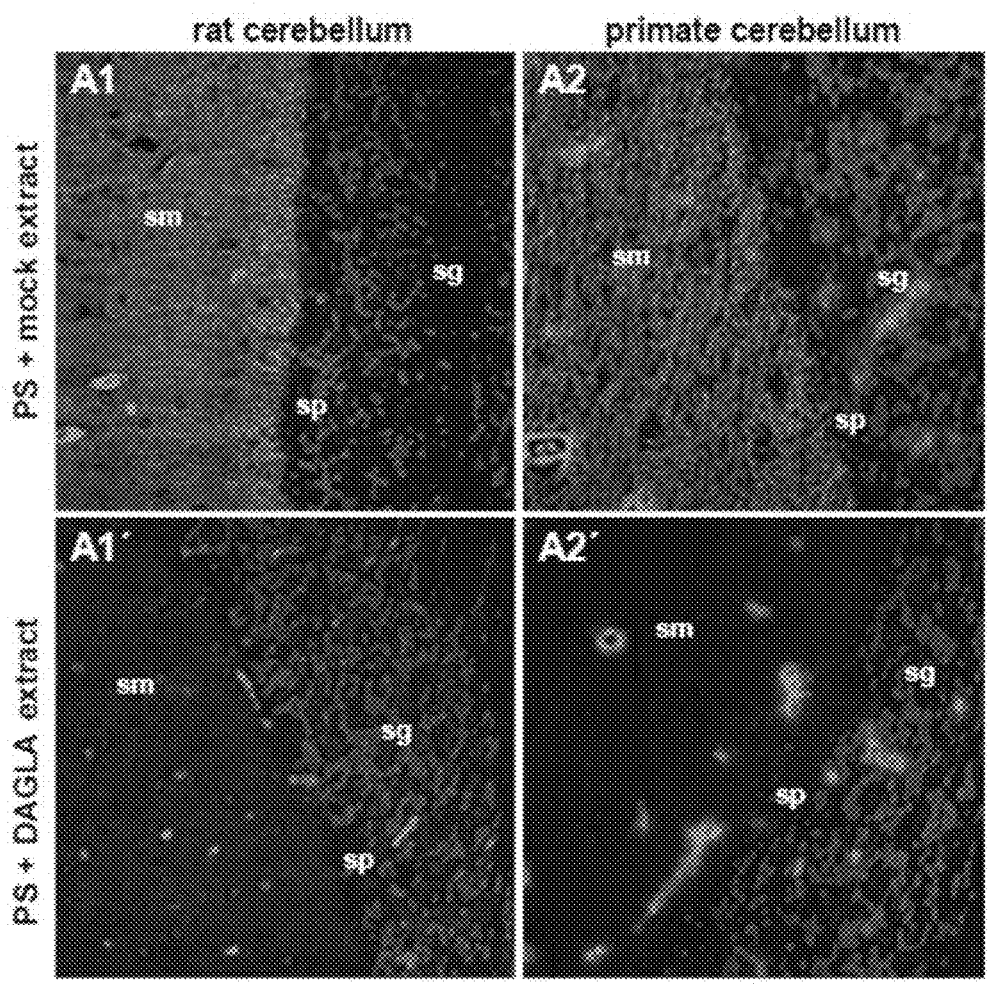
FIG. 3A shows the results of immunofluorescence on rat and primate cerebellum using autoantibodies from patients that were or were not pre-incubated with DAGLA. The reaction of the patients' auto-antibodies on tissue could be abolished by pre-incubation with HEK293 lysate containing DAGLA (SEQ ID NO 4). Antibody binding was unaffected when a comparable fraction from mock-transfected HEK293 cells was used.

FIG. 3 shows the results of immunofluorescence on rat and primate cerebellum using autoantibodies from patients that were or were not pre-incubated with DAGLA. The reaction of the patients' auto-antibodies on tissue could be abolished by pre-incubation with HEK293 lysate containing DAGLA (SEQ ID NO 4) (FIG. 3A). Antibody binding was unaffected when a comparable fraction from mock-transfected HEK293 cells was used.

Figure 3B:
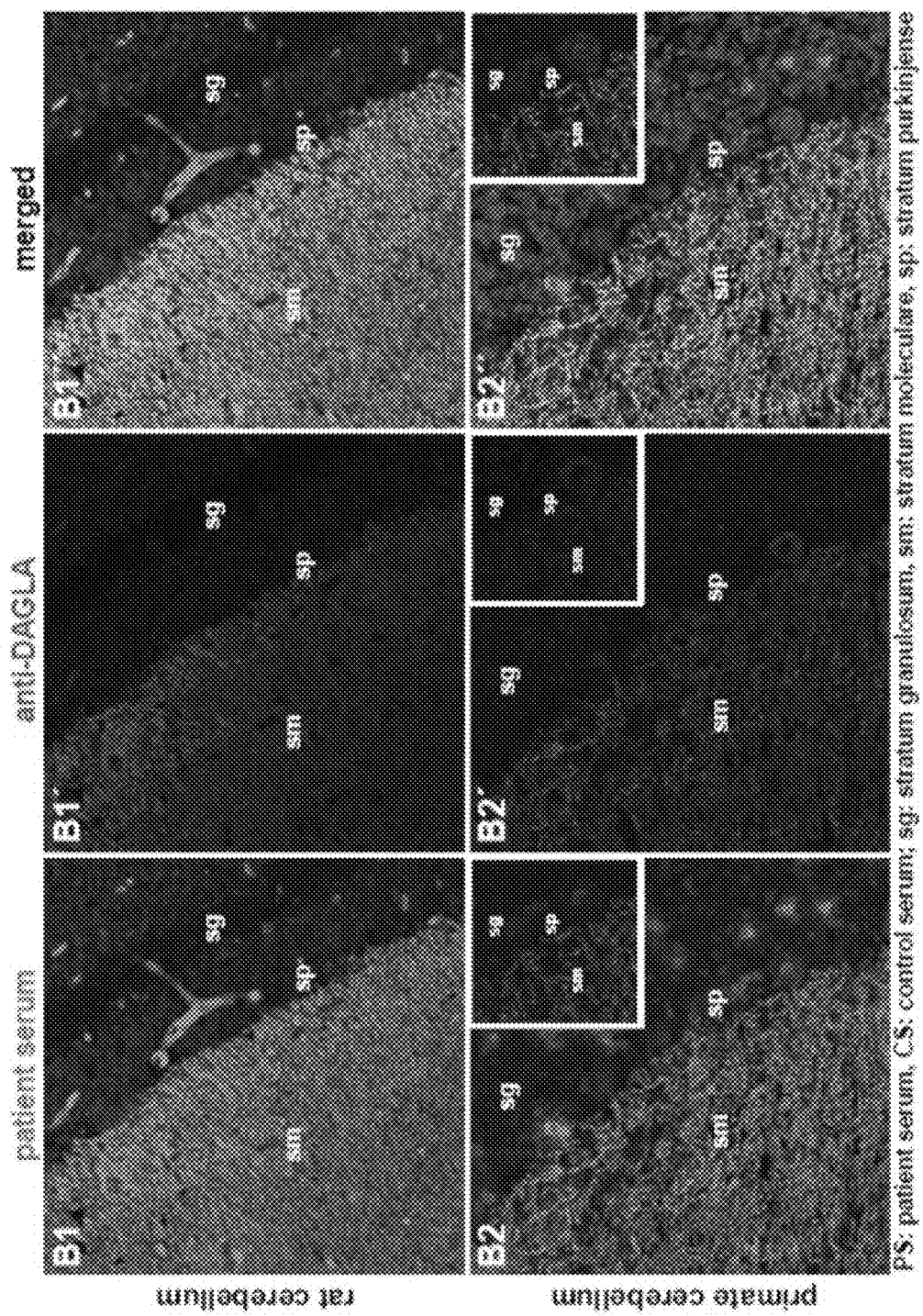
FIG. 3B shows indirect immunofluorescence with rat and primate cerebellum tissue using patient serum and a specific polyclonal anti-DAGLA antibody (Sigma-Aldrich, Germany) revealed an exact overlap of the molecular layer staining.

Indirect immunofluorescence with rat and primate cerebellum tissue using patient serum and a specific polyclonal anti-DAGLA antibody (Sigma-Aldrich, Germany) revealed an exact overlap of the molecular layer staining (FIG. 3B).

Figure 4:
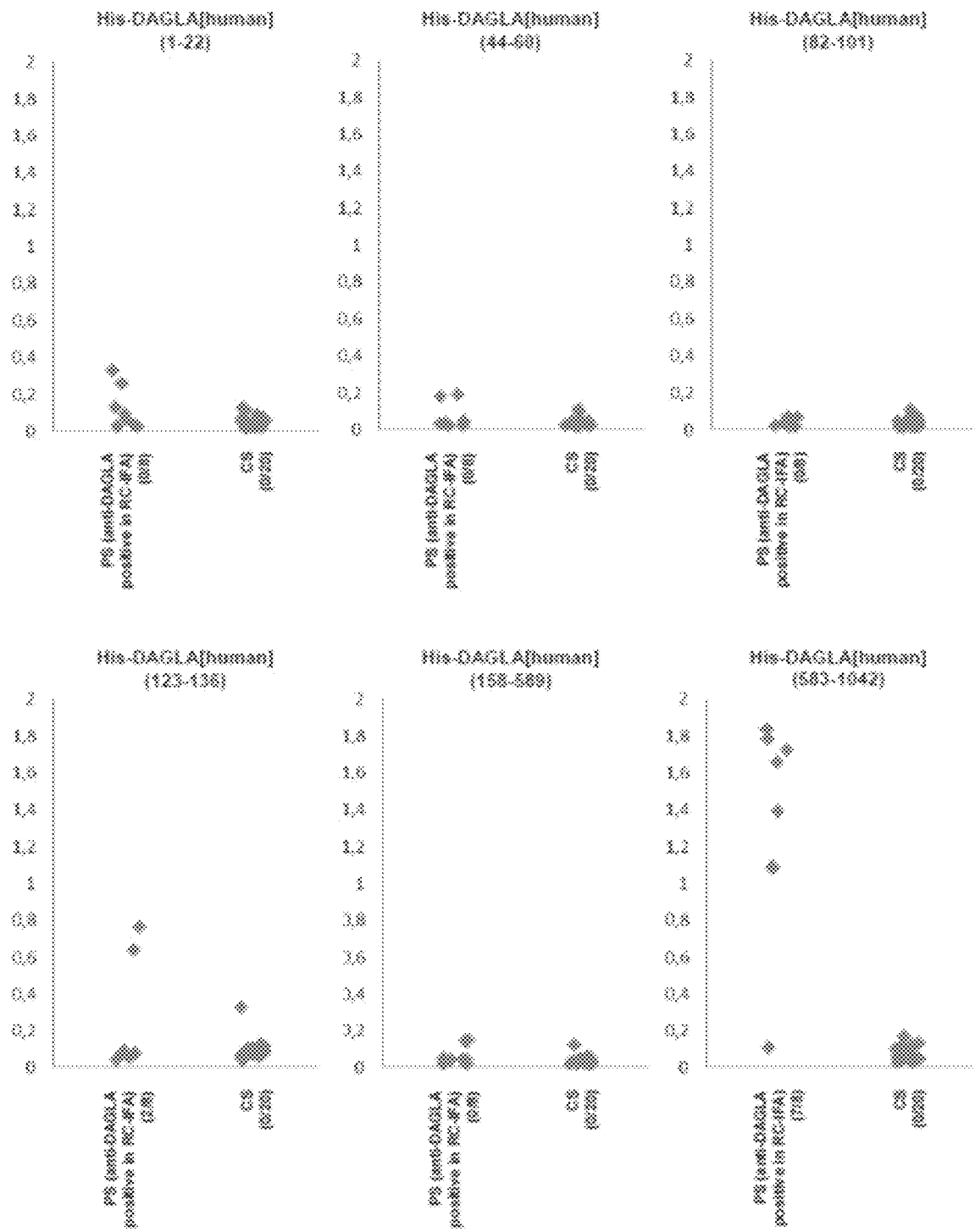
FIG. 4 shows an ELISA analysis of eight positive patient sera comprising autoantibodies to DAGLA using six different fragments of human DAGLA. Two fragments (583-1042 and 123-136) yielded positive results.

FIG. 4 shows an ELISA analysis of eight positive patient sera comprising autoantibodies to DAGLA using six different fragments of human DAGLA. Two fragments (583-1042 and 123-136) yielded positive results.

The present application comprises a range of sequences, more specifically:

(cDNA encoding human DAGLA)
SEQ ID NO 1
atgcccgggatcgtggtgttccggcggcgctggtctgtgggcagtgat gacctcgtcctaccagccatcttcctcttctcctgcataccacctgg tttgtgatcctgtccgtggtgctcttcggcctggtctataacccgcac gaggcctgctccctgaacctggtggaccacggccgcggctacctgggc atcctgctgagctgcatgatcgctgagatggccatcatctggctgagc atgcgcggggcatcctctacacggagccccgtgactccatgcagtac gtgctctacgtgcgcctggccatcctggtgatcgagttcatctacgcc atcgtgggcatcgtctggctcactcagtactacacctcctgcaacgac ctcactgccaagaatgtcaccctcggaatggttgtctgcaactgggta gtcatcctcagtgtgtgcatcactgtcctctgcgtcttcgaccccacg ggccgcacctttgtcaagctgagagccaccaagaggaggcagcgtaac ctgcggacctacaacctgcggcaccgcttagaggagggtcaagccacc agctggtcgcgccggctcaaagtgttcctctgctgcacgcggacgaag gactcccagtcagatgcctactcagaaatcgcctacctctttgcggag ttcttccgggaccttgacattgtgccatccgacatcattgctggcctg gtgctgctccggcagcggcagcgggccaagcgcaacgccgtgctggac gaggcaaacaatgacatcttggccttcctgtctgggatgccggtgacc -continued

```
agaaacaccaagtacctcgacctcaagaattcacaagagatgctccgc
tacaaagaggtctgctactacatgctctttgccctggctgcctacggg
tggcccatgtacctgatgcggaagcccgcctgcggcctctgccaactg
gctcggtcctgctcgtgttgcctgtgtcctgcgaggccgcggttcgcc
cctggagtcaccatcgaggaagacaactgctgtggctgtaatgccatt
gccatccggcgccacttcctggacgagaacatgactgcggtggacatc
gtctataccctgccatgatgcggtctatgaaacgccttctacgtg
gcggtggaccatgacaagaagaaagtggtgatcagtatccggggacc
ctgtccccaaggatgccctgactgacctgacgggtgatgctgagcgc
ctccccgtggagggcaccacggcacctggctgggccacaagggtatg
gtcctctcagctgagtacatcaagaagaaactggagcaggagatggtc
ctgtcccaggcctttgggcgagacctgggccgcggaaccaaacactac
ggcctgattgtggtgggccactccctgggcgcgggcactgctgccatc
ctctccttcttctgcgcccacagtatccgacccctcaagtgctttgcc
tactcccgccaggggcctgctgagtgaggatgcaatggagtattcc
aaggagttcgtgactgctgtggttctgggcaaagacctcgtccccagg
attggcctctctcagctggaaggcttccgcagacagctcctggatgtc
ctgcagcgaagcaccaagcccaatggcggatcatcgtggggccacc
aaatgcatccccaagtcggagctgcctgaggaggtagaggtgaccacc
ctggccagcacgcggctctggacccaccccagcgacctaactatagcc
ctctcagccagcactccactctacccgcccggccgcatcatccacgtg
gtccacaaccacctgcagagcagtgctgctgctgtgagcaggaggag
cccacatactttgccatctggggcgacaacaaggccttcaatgaggtg
atcatctcgccagccatgctgcatgagcacctgccctatgtggtcatg
gaggggctcaacaaggtgctggagaactacaacaaggggaagaccgct
ctgctctctgcagccaaggtcatggtgagccctaccgaggtggacctg
actcctgagctcatcttccagcagcagccactccccacggggccgccc
atgcccactggccttgccctggagctgccgactgcagaccaccgcaac
agcagcgtcaggagcaagtcccagtctgagatgagcctggagggcttc
tcggaggggcggctgctgtcgccagtggttgcggcggcggccgccag
gacccggtggagctgctgctgctgtctacccaggagcggctggcggcg
gagctgcaggcccggcgggcaccactggccaccatggagagcctctcg
gacactgagtccctgtacagcttcgactcgcgccgctcctcaggcttc
cgcagcatccggggctcccccagcctccacgctgtgctggagcgtgat
gaaggccacctcttctacattgaccctgccatccccgaggaaaaccca
tccctgagctcgcgcactgagctgctggccgccgacagcctgtccaag
cactcacaggacacgcagcccctggaggcgggcctgggcagtggcggc
gtcactcctgagcggccccccagtgctgcggccaatgacgaggaggaa
gaggttggcggtgggggtggcgggccggcctcccgcggggagctggcg
ctgcacaatgggcgcctgggggactcgcccagtcctcaggtgctggaa
ttcgccgagttcatcgacagcctcttcaacctggacagcaagagcagc
tccttccaagacctctactgcatggtggtgcccgagagccccaccagt
gactacgctgagggccccaagtcccccagccagcaagagatcctgctc
cgtgcccagttcgagcccaacctggtgcccaagcccccacggctctttt
gccggctcagccgaccccctcctcgggcatctcactctcgccctccttc
ccgctcagctcctcggtgagctcatggacctgacgcccacgggcctc
agtagccaggaatgcctggcggctgacaagatccggacttctacccc
actggccacggagccagccccgccaagcaagatgagctggtcatctca
gcacgctag
```

[sense DAGLA primer for amplifying cDNA]
SEQ ID NO 2
ATACGTCTCACATGCCCGGGATCGTGGTGTTCCGG

[antisense DAGLA-Stop primer for amplifying cDNA]
SEQ ID NO 3
ATACGTCTCCTCGAGCTAGCGTGCTGAGATGACCAGCTC (DAGLA as expressed in HEK293)
SEQ ID NO 4
MPGIVVFRRRWSVGSDDLVLPAIFLFLLHTTWFVILSVVLFGLVYNPH
EACSLNLVDHGRGYLGILLSCMIAEMAIIWLSMRGGILYTEPRDSMQY
VLYVRLAILVIEFIYAIVGIVWLTQYYTSCNDLTAKNVTLGMVVCNWV
VILSVCITVLCVFDPTGRTFVKLRATKRRQRNLRTYNLRHRLEEGQAT
SWSRRLKVFLCCTRTKDSQSDAYSEIAYLFAEFFRDLDIVPSDIIAGL
VLLRQRQRAKRNAVLDEANNDILAFLSGMPVTRNTKYLDLKNSQEMLR
YKEVCYYMLFALAAYGWPMYLMRKPACGLCQLARSCSCCLCPARPRFA
PGVTIEEDNCCGCNAIAIRRHFLDEMNITAVDIVYTSCHDAVYETPFY
VAVDHDKKKVVISIRGTLSPKDALTDLTGDAERLPVEGHHGTWLGHKG
MVLSAEYIKKKLEQEMVLSQAFGRDLGRGTKHYGLIVVGHSLGAGTAA
ILSFLLRPQYPTLKCFAYSPPGGLLSEDAMEYSKEFVTAVVLGKDLVP
RIGLSQLEGFRRQLLDVLQRSTKPKAVRIIVGATKCIPKSELPEEVEV
TTLASTRLWTHPSDLTIALSASTPLYPPGRIIHVVHNHPAEQCCCCEQ
EEPTYFAIWGDNKAFNEVIISPAMLHEHLPYVVMEGLNKVLENYNKGK
TALLSAAKVMVSPTEVDLTPELIFQQQPLPTGPPMPTGLALELPTADH
RNSSVRSKSQSEMSLEGFSEGRLLSPVVAAAARQDPVELLLLSTQERL
AAELQARRAPLATMESLSDTESLYSFDSRRSSGFRSIRGSPSLHAVLE
RDEGHLFYIDPAIPEENPSLSSRTELLAADSLSKHSQDTQPLEAALGS
GGVTPERPPSAAANDEEEEVGGGGGGPASRGELALHNGRLGDSPSPQV
LEFAEFIDSLFNLDSKSSSFQDLYCMVVPESPTSDYAEGPKSPSQQEI
LLRAQFEPNLVPKPPRLFAGSADPSSGISLSPSFPLSSSGELMDLTPT
GLSSQECLAADKIRTSTPTGHGASPAKQDELVISAR

[sense DAGLA[1-22] primer for cloning DAGLA fragment]
SEQ ID NO 5
CATGCCCGGGATCGTGGTGTTCCGGCGGCGCTGGTCTGTGGGCAGTGA
TGACCTCGTCCTACCAGCCTAATGA

[antisense DAGLA[1-22] primer for cloning DAGLA fragment]
SEQ ID NO 6
TCGATCATTAGGCTGGTAGGACGAGGTCATCACTGCCCACAGACCAGC
GCCGCCGGAACACCACGATCCCGGG

[sense DAGLA[44-60] primer for cloning DAGLA fragment]
SEQ ID NO 7
CATGGTCTATAACCCGCACGAGGCCTGCTCCCTGAACCTGGTGGACCA
CGGCCGCTAATGA

[antisense DAGLA[44-60] primer for cloning DAGLA fragment]
SEQ ID NO 8
TCGATCATTAGCGGCCGTGGTCCACCAGGTTCAGGGAGCAGGCCTCGT
GCGGGTTATAGAC

[sense DAGLA[81-101] primer for cloning DAGLA fragment]
SEQ ID NO 9
CATGCGCGGGGCATCCTCTACACGGAGCCCCGTGACTCCATGCAGTA
CGTGCTCTACGTGCGCTAATGA

[antisense DAGLA[81-101] primer for cloning DAGLA fragment]
SEQ ID NO 10
TCGATCATTAGCGCACGTAGAGCACGTACTGCATGGAGTCACGGGGCT
CCGTGTAGAGGATGCCCCCGCG

[sense DAGLA[123-136] primer for cloning DAGLA fragment]
SEQ ID NO 11
CATGTACACCTCCTGCAACGACCTCACTGCCAAGAATGTCACCCTCTA
ATGA

[antisense DAGLA[123-136] primer for cloning DAGLA fragment]
SEQ ID NO 12
TCGATCATTAGAGGGTGACATTCTTGGCAGTGAGGTCGTTGCAGGAGG
TGTA (H8-GST-DAGLA[1-22])
SEQ ID NO 13
MSHHHHHHHHMSPILGYWKIKGLVQPTRLLLEYLEEKYEEHLYERDEG
DKWRNKKFELGLEFPNLPYYIDGDVKLTQSMAIIRYIADKHNMLGGCP
KERAEISMLEGAVLDIRYGVSRIAYSKDFETLKVDFLSKLPEMLKMFE
DRLCHKTYLNGDHVTHPDFMLYDALDVVLYMDPMCLDAFPKLVCFKKR
IEAIPQIDKYLKSSKYIAWPLQGWQATFGGGDHPPKLEVLFQGPAMPG
IVVFRRRWSVGSDDLVLPA (H8-GST-DAGLA[44-60])
SEQ ID NO 14
MSHHHHHHHHMSPILGYWKIKGLVQPTRLLLEYLEEKYEEHLYERDEG
DKWRNKKFELGLEFPNLPYYIDGDVKLTQSMAIIRYIADKHNMLGGCP
KERAEISMLEGAVLDIRYGVSRIAYSKDFETLKVDFLSKLPEMLKMFE
DRLCHKTYLNGDHVTHPDFMLYDALDVVLYMDPMCLDAFPKLVCFKKR
IEAIPQIDKYLKSSKYIAWPLQGWQATFGGGDHPPKLEVLFQGPAMVY
NPHEACSLNLVDHGR (H8-GST-DAGLA[81-101])
SEQ ID NO 15
MSHHHHHHHHMSPILGYWKIKGLVQPTRLLLEYLEEKYEEHLYERDEG
DKWRNKKFELGLEFPNLPYYIDGDVKLTQSMAIIRYIADKHNMLGGCP
KERAEISMLEGAVLDIRYGVSRIAYSKDFETLKVDFLSKLPEMLKMFE
DRLCHKTYLNGDHVTHPDFMLYDALDVVLYMDPMCLDAFPKLVCFKKR
IEAIPQIDKYLKSSKYIAWPLQGWQATFGGGDHPPKLEVLFQGPAMRG
GILYTEPRDSMQYVLYVR (H8-GST-DAGLA[123-136])
SEQ ID NO 16
MSHHHHHHHHMSPILGYWKIKGLVQPTRLLLEYLEEKYEEHLYERDEG
DKWRNKKFELGLEFPNLPYYIDGDVKLTQSMAIIRYIADKHNMLGGCP
KERAEISMLEGAYEDIRYGVSRIAYSKDFETLKVDFLSKLPEMLKMFE
DRLCHKTYLNGDHVIHPDFMLYDALDVVLYMDPMCLDAFPKLVCFKKR
IEAIPQIDKYLKSSKYIAWPLQGWQATFGGGDHPPKLEVLFQGPAMYT
SCNDLTAKNVTL

[sense DAGLA[158-598]]
SEQ ID NO 17
ATACGTCTCGCATGGACCCCACGGGCCGCACCTTTGTCAAG

[antisense DAGLA[158-598]]
SEQ ID NO 18
TATCGTCTCGTCGATCATTATGGAGTGCTGGCTGAGAGGGCTATAG

[sense DAGLA[583-1042]]
SEQ ID NO 19
ATACGTCTCGCATGTGGACCCACCCCAGCGACCTAACTATAGC

[antisense DAGLA[583-1042]]
SEQ ID NO 20
TATCGTCTCGTCGATCATTAGCGTGCTGAGATGACCAGCTCATCTTG (H8-DAGLA[158-598])
SEQ ID NO 21
MSHHHHHHHHSMDPTGRTFVKLRATKRRQRNLRTYNLRHRLEEGQATS
WSRRLKVFLCCTRTKDSQSDAYSEIAYLFAEFFRDLDIVPSDIIAGLV
LLRQRQRAKRNAVLDEANNDILAFLSGMPVTRNTKYLDLKNSQEMLRY
KEVCYYMLFALAAYGWPMYLMRKPACGLCQLARSCSCCLCPARPRFAP
GVTIEEDNCCGCNAIAIRRHFLDENMTAVDIVYTSCHDAVYETPFYVA
VDHDKKKVVISIRGTLSPKDALTDLTGDAERLPVEGHHGTWLGHKGMV
LSAEYIKKKLEQEMVLSQAFGRDLGRGTKHYGLIVVGHSLGAGTAAIL
SFLLRPQYPTLKCFAYSPPGGLLSEDAMEYSKEFVTAVVLGKDLVPRI
GLSQLEGFRRQLLDVLQRSTKPKWRIIVGATKCIPKSELPEEVEVTTL
ASTRLWTHPSDLTIALSASTP (H8-DAGLA[583-1042])
SEQ ID NO 22
MSHHHHHHHHSMWTHPSDLTIALSASTPLYPPGRIIHVVHNHPAEQCC
CCEQEEPTYFAIWGDNKAFNEVIISPAMLHEHLPYVVMEGLNKVLENY
NKGKTALLSAAKVMVSPTEVDLTPELIFQQQPLPTGPPMPTGLALELP
TADHRNSSVRSKSQSEMSLEGFSEGRLLSPVVAAAARQDPVELLLLST
QERLAAELQARRAPLATMESLSDTESLYSFDSRRSSGFRSIRGSPSLH
AVLERDEGHLFYIDPAIPEENPSLSSRTELLAADSLSKHSQDTQPLEA -continued
ALGSGGVTPERPPSAAANDEEEEVGGGGGGPASRGELALHNGRLGDSP

SPQVLEFAEFIDSLFNLDSKSSSFQDLYCMVVPESPTSDYAEGPKSPS

QQEILLRAQFEPNLVPKPPRLFAGSADPSSGISLSPSFPLSSSGELMD

LTPTGLSSQECLAADKIRTSTPTGHGASPAKQDELVISAR (H8-GST-DAGLA[1-22])
                                                 SEQ ID NO 23
MPGIVVFRRRWSVGSDDLVLPA (H8-GST-DAGLA[44-60])
                                                 SEQ ID NO 24
VYNPHEACSLNLVDHGR (H8-GST-DAGLA[81-101])
                                               SEQ ID NO 25
MRGGILYTEPRDSMQYVLYVR (H8-GST-DAGLA[123-136]), reactive with patient
sera
                                               SEQ ID NO 26
YTSCNDLTAKNVTL (DAGLA[158-598])
                                               SEQ ID NO 27
TGRTFVKLRATKRRQRNLRTYNLRHRLEEGQATSWSRRLKVFLCCTRT

KDSQSDAYSEIAYLFAEFFRDLDIVPSDIIAGLVLLRQRQRAKRNAVL

DEANNDILAFLSGMPVTRNTKYLDLKNSQEMLRYKEVCYYMLFALAAY

GWPMYLMRKPACGLCQLARSCSCCLCPARPRFAPGVTIEEDNCCGCNA

IAIRRHFLDENMTAVDIVYTSCHDAVYETPFYVAVDHDKKKVVISIRG

TLSPKDALTDLTGDAERLPVEGHHGTWLGHKGMVLSAEYIKKKLEQEM

VLSQAFGRDLGRGTKHYGLIVVGHSLGAGTAAILSFLLRPQYPTLKCF

AYSPPGGLLSEDAMEYSKEFVTAVVLGKDLVPRIGLSQLEGFRRQLLD

VLQRSTKPKWRIIVGATKCIPKSELPEEVEVTTLASTRLWTHPSDLTI

ALSASTPPD (DAGLA[583-1042]), reactive with patient sera
                                               SEQ ID NO 28
WTHPSDLTIALSASTPLYPPGRIIHVVHNHPAEQCCCCEQEEPTYFAI

WGDNKAFNEVIISPAMLHEHLPYVVMEGLNKVLENYNKGKTALLSAAK

VMVSPTEVDLTPELIFQQQPLPTGPPMPIGLALELPTADHRNSSVRSK

SQSEMSLEGFSEGRLLSPVVAAAARQDPVELLLLSTQERLAAELQARR

APLATMESLSDTESLYSFDSRRSSGFRSIRGSPSLHAVLERDEGHLFY

IDPAIPEENPSLSSRTELLAADSLSKHSQDTQPLEAALGSGGVTPERP

PSAAANDEEEEVGGGGGGPASRGELALHNGRLGDSPSPQVLEFAEFID

SLFNLDSKSSSFQDLYCMVVPESPTSDYAEGPKSPSQQEILLRAQFEP

NLVPKPPRLFAGSADPSSGISLSPSFPLSSSGELMDLTPTGLSSQECL

AADKIRTSTPTGHGASPAKQDELVISAR

The present invention is further illustrated by the following non-limiting examples from which further features, embodiments, aspects and advantages of the present invention may be taken.

Examples

SUMMARY

Methods:

Five patients (P1-P5) suffering from neurological conditions underwent serological investigation. For this purpose, sera from all five patients were subjected to comprehensive autoantibody screening by indirect immunofluorescence assay (IFA) and immunoblot. Immunoprecipitation with lysates of cerebellum followed by mass spectrometry (MS) was used to identify the autoantigen, which was verified by Western blot (WB) with monospecifc animal antibody against the respective target antigen as well as by recombinant expression in HEK293 cells and use of the recombinant protein in immunoassays. Furthermore, sera of patients with neurological symptoms and defined anti-neural autoantibodies, sera with a similar staining pattern as P1 to P5 without known autoantibody reactivity, as well as negative control sera were screened for anti-DAGLA antibodies. Six different fragments of the DAGLA protein were recombinantly expressed in E. coli. Purified proteins were analyzed in ELISA using anti-DAGLA positive patient sera and healthy controls.

Results:

IFA screening of sera from P1 to P5 revealed IgG reactivity with the molecular layer in rodent and monkey cerebellum. The dendrites of the purkinje cells are stained while the purkinje cell somata do not react. Furthermore, no IgG reactivity was found with a panel of 30 recombinantly expressed established neural autoantigens. The sera of P1 to P5 immunoprecipitated Sn1-specific diacylglycerol lipase alpha (DAGLA), as detected by Coomassie-stained SDS-PAGE followed by MALDI-TOF mass spectrometry. When the immunoprecipitates were analyzed by Western blot using a monospecifc animal antibody against DAGLA, anti-DAGLA showed reactivity with the immunoprecipitate of P1 to P5 while there was no reactivity in the immunoprecipitates of five control sera. However, in the sera of P1 to P5 as well as in seven additional patient sera (P6 to P12) with a similar staining pattern on cerebellum anti-DAGLA antibodies could be detected by RC-IFA with the recombinant protein. Screening of healthy control sera without a specific reaction in IIFT with neuronal tissues (n=51) revealed no anti-DAGLA positive samples. ELISA using recombinantly expressed fragments of the human DAGLA protein revealed the main reactivity of the anti-DAGLA positive sera with the c-terminal intracellular fragment.

Clinical data from two of the patients with anti-DAGLA autoantibodies were available. P11 suffered from cerebellitis and P12 suffered from epilepsy and hippocampus sclerosis.

Patients

Control collectives included 51 healthy donors and 40 patients with neurological symptoms and defined anti-neural autoantibodies (3× anti-CASPR2, 5× anti-NMDAR, 5× anti-LGI1, 5× anti-Hu, 2× anti-Hu/anti-Ri 3× anti-Ri, 2× anti-Yo/anti-Ri, 3× anti-Yo, 5× anti-AQP4, 5× anti-GAD65, 2× anti-GABAB receptor).

Indirect Immunofluorescence Assay (IFA)

IFA was conducted using slides with a biochip array of brain tissue cryosections (hippocampus of rat, cerebellum of rat and monkey) combined with recombinant HEK293 cells separately expressing 30 different brain antigens Hu, Yo, Ri, CV2, PNMA2, ITPR1, Homer 3, CARP VIII, ARHGAP26, ZIC4, DNER/Tr, GAD65, GAD67, amphiphysin, recoverin, $GABA_B$ receptor, glycine receptor, DPPX, IgLON5, glutamate receptors (types NMDA, AMPA, mGluR1, mGluR5, GLURD2), LGI1, CASPR2, AQP4 (M1 and M23), MOG, ATP1A3, NCDN (EUROIMMUN, FA 111a-1003-51, FA 1112-1003-50, FA-1128-1003-50, FA112d-1003-1, FA 112m-1003-50, FA 1151-1003-50, Miske R, Hahn S, Rosenkranz T, Müller M, Dettmann I M, Mindorf S, Denno Y, Brakopp S, Scharf M, Teegen B, Probst C, Melzer N, Meinck H M, Terborg C, Stöcker W, Komorowski L., 2016, Autoantibodies against glutamate receptor δ2 after allogenic stem cell transplantation. Neurol Neuroimmunol Neuroinflamm., 3(4):e255; Scharf M, Miske R, Heidenreich F, Giess R, Landwehr P, Blöcker I M, Begemann N, Denno Y, Tiede S, Däihnrich C, Schlumberger W, Unger M, Teegen B, Stöcker W, Probst C, Komorowski L, 2015, Neuronal Na+/K+ ATPase is an autoantibody target in paraneoplastic neurologic syndrome, Neurology; 84(16):1673-9; Miske R, Gross C C, Scharf M, Golombeck K S, Hartwig M, Bhatia U, Schulte-Mecklenbeck A, Bönte K, Strippel C, Schöls L, Synofzik M, Lohmann H, Dettmann I M, Deppe M, Mindorf S, Warnecke T, Denno Y, Teegen B, Probst C, Brakopp S, Wandinger K P, Wiendl H, Stöcker W, Meuth S G, Komorowski L, Melzer N, 2016, Neurochondrin is a neuronal target antigen in autoimmune cerebellar degeneration, Neurol Neuroimmunol Neuroinflamm.; 4(1):e307)). Each biochip mosaic was incubated with 70 µL of PBS-diluted sample at room temperature for 30 min, washed with PBS-Tween and immersed in PBS-Tween for 5 min. In the second step, either Alexa488-labelled goat anti-human IgG (Jackson Research, Suffolk, United Kingdom), or fluorescein isothiocyanate (FITC)-labelled goat anti-human IgG (EUROIMMUN Medizinische Labordiagnostika AG, Lübeck) were applied and incubated at room temperature for 30 min. Slides were washed again with a flush of PBS-Tween and then immersed in PBS-Tween for 5 min. Slides were embedded in PBS-buffered, DABCO containing glycerol (approximately 20 µL per field) and examined by fluorescence microscopy. Positive and negative controls were included. Samples were classified as positive or negative based on fluorescence intensity of the transfected cells in direct comparison with non-transfected cells and control samples. Endpoint titers refer to the last dilution showing visible fluorescence.

Results were evaluated by two independent observers using a EUROSTARII microscope (EUROIMMUN Medizinische Labordiagnostika AG, Lübeck, Germany). Reagents were obtained from Merck, Darmstadt, Germany or Sigma-Aldrich, Heidelberg, Germany if not specified otherwise.

Immunoblot

Immunoprecipitated cerebellum lysate were incubated with NuPage LDS sample buffer (ThermoFisher Scientific, Schwerte, Germany) containing 25 mmol/L dithiothreitol at 70° C. for 10 minutes, followed by SDS-PAGE (NuPAGE, ThermoFisher Scientific, Schwerte, Germany). Separated proteins were electro-transferred onto a nitrocellulose membrane by tank blotting with transfer buffer (ThermoFisher Scientific) according to the manufacturer's instructions. The membranes were blocked with Universal Blot Buffer plus (EUROIMMUN Medizinische Labordiagnostika AG, Lübeck) for 15 min and incubated with the patient or control sera (dilution 1:200) or monospecific rabbit antibody against DAGLA (Sigma Aldrich, HPA062497, 1:2,000) in Universal Blot Buffer plus for 3 hours, followed by 3 washing steps with Universal Blot Buffer (EUROIMMUN Medizinische Labordiagnostika AG, Lübeck), a second incubation for 30 min with anti-human-IgG-AP (EUROIMMUN Medizinische Labordiagnostika AG, Lübeck, 1:10) or anti-rabbit-IgG-AP (1:2,000) in Universal Blot Buffer plus, 3 washing steps, and staining with NBT/BCIP substrate (EUROIMMUN Medizinische Labordiagnostika AG, Lübeck). Reagents were obtained from Merck, Darmstadt, Germany or Sigma-Aldrich, Heidelberg, Germany if not specified otherwise.

Identification of the Antigens

Cerebellum from rat was dissected and shock-frozen in liquid nitrogen. The tissues were homogenised in solubilization buffer (100 mmol/L tris-HCl pH 7.4, 150 mmol/L sodium chloride, 2.5 mmol/L ethylenediamine tetraacetic acid, 0.5% (w/v) sodium deoxycholate, 1% (w/v) Triton X-100) containing protease inhibitors (Complete mini, Roche Diagnostics, Penzberg, Germany) with a Miccra D-8 (Roth, Karlsruhe, Germany) and a hand homogenizer (Sartorius, Göttingen, Germany) at 4° C. The tissue lysates were centrifuged at 21,000×g at 4° C. for 15 min and clear supernatants were incubated with patient's serum (diluted 1:16,7) at 4° C. overnight. The samples were then incubated with Protein G Dynabeads (ThermoFisher Scientific, Dreieich, Germany) at 4° C. for 3 h to capture immunocomplexes. Beads were washed 3 times with PBS, and eluted with NuPage LDS sample buffer (ThermoFisher Scientific, Schwerte, Germany) containing 25 mmol/L dithiothreitol at 70° C. for 10 min. Carbamidomethylation with 59 mM iodoacetamide (Bio-Rad, Hamburg, Germany) was performed prior to SDS-PAGE (NuPAGE, ThermoFisher Scientific, Schwerte, Germany). Separated proteins were visualized with Coomassie Brilliant Blue (G-250) (Merck), and identified by mass spectrometric analysis.

Mass Spectrometry

Visible protein bands were excised from Coomassie Brilliant Blue G-250 stained gels. After destaining and tryptic digestion peptides were extracted and spotted with α-cyano-4-hydroxycinnamic acid onto an MTP AnchorChip™ 384 TF target.

MALDI-TOF/TOF measurements were performed with an Autoflex III smartbeam TOF/TOF200 System using flexControl 3.4 software. MS spectra for peptide mass fingerprinting (PMF) were recorded in positive ion reflector mode with 4,000-10,000 shots and in a mass range from 600 Da to 4,000 Da. Spectra were calibrated externally with the commercially available Peptide Calibration Standard II, processed with flexAnalysis 3.4 and peak lists were analyzed with BioTools 3.2.

The Mascot search engine Mascot Server 2.3 (Matrix Science, London, UK) was used for protein identification by searching against the NCBI or SwissProt database limited to Mammalia. Search parameters were as follows: Mass tolerance was set to 80 ppm, one missed cleavage site was accepted, and carbamidomethylation of cysteine residues as well as oxidation of methionine residues were set as fixed and variable modifications, respectively. To evaluate the protein hits, a significance threshold of $p<0.05$ was chosen.

For further confirmation of the PMF hits two to five peptides of each identified protein were selected for MS/MS measurements using the WARP feedback mechanism of BioTools. Parent and fragment masses were recorded with 400 and 1000 shots, respectively. Spectra were processed and analyzed as described above with a fragment mass tolerance of 0.7 Da.

Recombinant Expression of DAGLA in HEK293

The cDNA encoding human DAGLA (SEQ ID NO 1) was obtained from Source BioScience UK Limited as clone IRATp970E05140D. By PCR the coding sequence was amplified using the primers sense DAGLA (SEQ ID NO 2) and antisense DAGLA (SEQ ID NO 3). The amplification products were digested with BsmBI and ligated with NcoI and XhoI linearized pTriEx-1 (Merck, Darmstadt, Germany). The resulting construct coded SEQ ID NO 4.

DAGLA was transiently expressed in the human cell line HEK293 following PEI-mediated transfection (Exgene 500), according to the manufacturer's instructions (Biomol GmbH, Hamburg, Germany). The cells were harvested 5 days after transfection and lysed by ultrasound. The lysates were stored in aliquots at −80° C. until further use.

Recombinant Expression of DAGLA-Fragments in E. coli

For the expression of DAGLA fragments spanning amino acid residues 1 to 22, 44 to 60, 81 to 101, and 123 to 136 the coding sequence was generated by hybridization of oligodeoxynucleotides sense DAGLA[1-22] and antisense DAGLA [1-22] (SEQ ID NO 5 and 6), sense DAGLA[44-60] and antisense DAGLA[44-60] (SEQ ID NO 7 and 8), sense DAGLA[81-101] and antisense DAGLA[81-101] (SEQ ID NO 9 and 10) and sense DAGLA[123-136] and antisense DAGLA[123-136] (SEQ ID NO 11 and 12).

The linker fragments were fused to the octa Histidine (H8) tag and glutathione S-transferase (GST) tag coding sequence by ligation into a modified pET24d (Merck, Darmstadt, Germany) plasmid vector. These constructs encode H8-GST-DAGLA[1-22] (SEQ ID NO 13), H8-GST-DAGLA[44-60] (SEQ ID NO 14), H8-GST-DAGLA[81-101] (SEQ ID NO 15) and H8-GST-DAGLA[123-136] (SEQ ID NO 16) respectively.

The DAGLA[158-598] and DAGLA[583-1042] coding sequence was PCR amplified using human DAGLA cDNA (SEQ ID NO 1) and DNA oligonucleotides sense DAGLA [158-598] and antisense DAGLA[158-598] (SEQ ID NO 17 and 18)and sense DAGLA[583-1042] antisense DAGLA [583-1042] (SEQ ID NO 19 and 20) respectively. The amplification products were digested with BsmBI and integrated into NcoI XhoI linearized pET24d-N (Exp Dermatol. 2007 Sep.; 16(9):770-7) encoding H8-DAGLA[158-598] and H8-DAGLA[583-1042] (octa Histidine tag, H8) (SEQ ID NO 21 and 22 respectively).

Bacterial expression was essentially performed as described in the pET system manual (Merck, Darmstadt, Germany) employing E. coli strain RosettaBlue(DE3)pLacI (Merck, Darmstadt, Germany). Protein expression was induced by the addition of 2 mM isopropyl β-D-thiogalactoside (IPTG) for 3 hours at 37° C.

Purification:

Bacterial cells were lysed, and proteins were solubilized in urea buffer and purified by Ni2+-affinity chromatography following the protocol as in C. Probst, W. Schlumberger, W. Stocker et al., "Development of ELISA for the specific determination of autoantibodies against envoplakin and periplakin in paraneoplastic pemphigus," Clinica Chimica Acta, vol. 410, no. 1-2, pp. 13-18, 2009. The proteins were stored in aliquots at −80° C. until further use.

Characterization of the Patients' Autoantibodies

Indirect immunofluorescence assays (IFA) of sera P1 to P5 using permeabilized cryosections of rat and primate cerebellum showed granular staining of the molecular layer (FIG. 1). Further monospecific analyses were conducted with recombinant HEK293 cells expressing 30 neural autoantigens: Hu, Yo, Ri, CV2, PNMA2, SOX1, ITPR1, Homer 3, CARP VIII, ARHGAP26, ZIC4, DNER/Tr, GAD65, GAD67, amphiphysin, recoverin, GABAB receptor, glycine receptor, DPPX, IgLON5, glutamate receptors (types NMDA, AMPA, mGluR1, mGluR5, GLURD2), LGI1, CASPR2, AQP4 (M1 and M23), MOG, ATP1A3 and NCDN. No specific reactivity was observed.

Identification of DAGLA as the Target Neuronal Autoantigen

The immunoprecipitates from homogenized rat cerebellum obtained with P1 to P5 were subjected to Western Blot analysis. After incubation with the identical serum used for immunoprecipitation specific reactions of approximately 115 kDa were observed which were absent in the immunoprecipitates of the control sera (FIG. 2, A1). In Coomassie-stained SDS-PAGE slight bands could be detected at 115 kDa (FIG. 2, A2). Using MALDI-TOF MS, the protein was identified as DAGLA (UNIPROT acc. # Q5YLM1). As a proof for correct antigen identification, immunoprecipitates were tested by Western blot using antibodies against DAGLA. The immunoprecipitates of the patients' sera contained DAGLA as demonstrated by a 115 kDa band (FIG. 2, A3). Furthermore, the patients' samples were tested by IFA using transfected HEK293 cells which expressed DAGLA (SEQ ID NO 4). Patients' sera reacted with the DAGLA-expressing cells (FIG. 2 B1). In contrast, mock-transfected cell did not demonstrate any specific antibody binding (FIG. 2 B2).

The reaction of the patients' auto-antibodies on tissue could be abolished by pre-incubation with HEK293 lysate containing DAGLA (SEQ ID NO 4) (FIG. 3A). Antibody binding was unaffected when a comparable fraction from mock-transfected HEK293 cells was used.

IIFT with rat and primate cerebellum tissue using patient serum and a specific polyclonal anti-DAGLA antibody (Sigma-Aldrich, Germany) revealed an exact overlap of the molecular layer staining (FIG. 3B).

Specificity of Anti-DAGLA Auto-Antibodies

Sera from 40 patients with various neural auto-antibody-associated neurological syndromes (3× anti-CASPR2, 5× anti-NMDAR, 5× anti-LGI1, 5× anti-Hu, 2× anti-Hu/anti-Ri 3× anti-Ri, 2× anti-Yo/anti-Ri, 3× anti-Yo, 5× anti-AQP4, 5× anti-GAD65, 2× anti-GABAB receptor), and 51 healthy controls were analyzed by IFA with HEK293-DAGLA in parallel to the samples of the patients. None of the disease control or healthy control sera showed a positive reaction with the HEK293-DAGLA cells.

Immunoassay for the Detection of Autoantibodies with DAGLA Fragments

Ninety-six-well plates (Nunc, Germany) were coated with 100 μl of the recombinant protein at a concentration of 2,5 μg/ml in PBS for 2 h at 25° C., washed three times with washing buffer (0.05% [wt/vol] Tween 20 in PBS), and then blocked with blocking buffer (0.1% [wt/vol] casein in PBS) for 1 h. The success of antigen immobilization was confirmed by incubation with a murine monoclonal anti-hexahistidine tag antibody (Sigma-Aldrich, Germany) diluted 1:2,000. Experimental serum samples were diluted in sample buffer (1% [wt/vol] casein, 0.05% [wt/vol] Tween 20 in PBS) 1:100 and incubated for 30 min at room temperature. After washing three times, bound antibodies were detected by incubation with anti-mouse IgG-HRP conjugate (Jackson Research, UK) diluted 1:16,000 in sample buffer or anti-human IgG-POD undiluted (Euroimmun, Germany), for 30 min, washed as described above, and incubated with tetramethyl benzidine (TMB) substrate (Euroimmun, Germany) for 15 min. All incubation steps were carried out at room temperature. The optical density (OD) at 450 nm was read using an automated spectrophotometer (Tecan, Germany).

Eight patient sera, which showed a positive reaction in RC-IFA with HEK293-DAGLA and 20 healthy control sera were analyzed by ELISA using six different fragments of the human DAGLA protein (SEQ ID NO 13, 14, 15, 16, 21, 22) (FIG. 4). None of the patient sera or control sera showed a positive reaction with the fragments comprising AA 1-22

(SEQ ID NO 23), 44-60 (SEQ ID NO 24), 81-101 (SEQ ID NO 25), and 158-589 (SEQ ID NO 27). Seven patient sera showed a positive reaction with the c-terminal intracellular fragment AA 583-1042 (SEQ ID NO 28) while all of the control sera were negative. Two patient sera additional showed a positive reaction with the extracellular fragment 123-136 (SEQ ID NO 26) which was not observed with the control sera.

The invention claimed is:

1. A method, comprising:

contacting a patient sample to a peptide comprising
 (i) diacylglycerol lipase alpha (DAGLA) according to the amino acid sequence of SEQ ID NO: 4,
 (ii) the amino acid sequence according to SEQ ID NO: 26 or SEQ ID NO: 28, or
 (iii) a variant of DAGLA having at least 95% identity to the amino acid sequence of SEQ ID NO: 4, wherein the variations occur in the amino acid sequence according to SEQ ID NO: 23, SEQ ID NO: 24, SEQ ID NO: 25, or SEQ ID NO: 27, wherein the peptide comprising DAGLA, the amino acid sequence according to SEQ ID NO: 26 or SEQ ID NO: 28, or the variant of DAGLA is immobilized on a solid support, and detecting, in a sample from the patient, an autoantibody binding to DAGLA, the amino acid sequence according to SEQ ID NO: 26 or SEQ ID NO: 28, or the variant of DAGLA.

2. A method, comprising:
detecting the autoantibody to DAGLA according to claim 1.

3. The method according to claim 1, wherein the patient has or is suspected of having a disease selected from the group consisting of paraneoplastic neurological syndrome, cerebellitis, epilepsy, sclerosis and a tumor.

4. The method according to claim 1, wherein the sample is a bodily fluid comprising antibodies.

5. The method according to claim 1, wherein the autoantibody is detected using at least one technique selected from the group consisting of immunodiffusion techniques, immunoelectrophoretic techniques, light scattering immunoassays, agglutination techniques, labeled immunoassays chemiluminescence immunoassays, and immunofluorescence.

6. The method according to claim 1, wherein the DAGLA peptide or the variant thereof comprises at least 98% identity to SEQ ID NO: 1.

* * * * *